(12) United States Patent
Buckingham et al.

(10) Patent No.: US 9,227,014 B2
(45) Date of Patent: Jan. 5, 2016

(54) KALMAN FILTER BASED ON-OFF SWITCH FOR INSULIN PUMP

(71) Applicants: Bruce A. Buckingham, Palo Alto, CA (US); B. Wayne Bequette, Albany, NY (US); Fraser Cameron, Palo Alto, CA (US); Darrell M. Wilson, Sunnyvale, CA (US); H. Peter Chase, Denver, CO (US); Francis J. Doyle, III, Santa Barbara, CA (US); Matthew Stenerson, Daly City, CA (US)

(72) Inventors: Bruce A. Buckingham, Palo Alto, CA (US); B. Wayne Bequette, Albany, NY (US); Fraser Cameron, Palo Alto, CA (US); Darrell M. Wilson, Sunnyvale, CA (US); H. Peter Chase, Denver, CO (US); Francis J. Doyle, III, Santa Barbara, CA (US); Matthew Stenerson, Daly City, CA (US)

(73) Assignees: The Board of Trustees of the Laland Stanford Junior University, Palo Alto, CA (US); The Regents of the University of California, a California Corporation, Oakland, CA (US); The Regents of the University of Colorado, a body corporate, Denver, CO (US); Rensselaer Polytechnic Institute, Troy, NY (US)

(*) Notice: Subject to any disclaimer, the term of this patent is extended or adjusted under 35 U.S.C. 154(b) by 0 days.

(21) Appl. No.: 14/175,020

(22) Filed: Feb. 7, 2014

(65) Prior Publication Data
US 2014/0221966 A1   Aug. 7, 2014

Related U.S. Application Data

(60) Provisional application No. 61/762,300, filed on Feb. 7, 2013.

(51) Int. Cl.
*A61M 5/172* (2006.01)
*A61M 5/142* (2006.01)

(52) U.S. Cl.
CPC ......... *A61M 5/1723* (2013.01); *A61M 5/14244* (2013.01); *A61M 2005/14296* (2013.01);

(Continued)

(58) Field of Classification Search
CPC .......... A61M 5/1723; A61M 5/16881; A61M 5/1726; A61M 5/14244; A61M 2005/14296; A61M 2205/332; A61M 2230/201; A61M 2230/63; A61M 2230/005; A61M 2230/006; A61B 5/47225; A61B 5/411
USPC ........................................ 604/504, 65, 66, 67
See application file for complete search history.

(56) References Cited

U.S. PATENT DOCUMENTS 6,572,545 B2 * 6/2003 Knobbe et al. ................ 600/365
6,873,268 B2   3/2005 Lebel et al.

(Continued)

OTHER PUBLICATIONS

Eran Atlas et al., "MD-Logic Artificial Pancreas System: A pilot study in adults with type-1 diabetes", "Diabetes Care", 2010, vol. 33, No. 5, Publisher: The American Diabetes Association, Published in: care. diabetesjournals.org.

(Continued)

*Primary Examiner* — Kami A Bosworth
*Assistant Examiner* — Hamza Darb
(74) *Attorney, Agent, or Firm* — Eugene J. Molinelli; Beusse Wolter Sanks & Maire PLLC

(57) ABSTRACT

Techniques for controlling an insulin pump include determining values for parameters selected from a group including a first prediction time horizon, a predicted glucose threshold (Goff) for turning the insulin pump off, a maximum shut off time within a time window, and duration of the time window. A safety rule is determined based on the maximum shut off time within the duration. Glucose readings are collected up to a current time. An expected current glucose value G and glucose temporal rate of change are determined based only on the glucose readings and a Kalman filter configured for noisy glucose readings. A glucose level (Gh1) is predicted for a future time that is the prediction time horizon after the current time. A command is issued to shut off the insulin pump if it is determined both that Gh1 is less than Goff and that the safety rule is satisfied.

17 Claims, 11 Drawing Sheets

(52) U.S. Cl.
CPC .... *A61M2205/332* (2013.01); *A61M 2230/005* (2013.01); *A61M 2230/06* (2013.01); *A61M 2230/201* (2013.01); *A61M 2230/63* (2013.01)

(56) References Cited

U.S. PATENT DOCUMENTS

| | | | |
|---|---|---|---|
| 2005/0171503 A1 | 8/2005 | Van Den Berghe et al. | |
| 2008/0058625 A1 | 3/2008 | McGarraugh et al. | |
| 2008/0257412 A1* | 10/2008 | Gordon | 137/8 |
| 2010/0295686 A1* | 11/2010 | Sloan et al. | 340/573.1 |
| 2012/0059353 A1* | 3/2012 | Kovatchev et al. | 604/504 |

OTHER PUBLICATIONS

Bruce Buckingham et al., "Preventing Hypoglycemia Using Predictive Alarm Algorithms and Insulin Pump Suspension", "Diabetes Technology and Therapeutics", 2009, pp. 93-97, vol. 11, No. 2, Publisher: Mary Ann Liebert, Inc., Published in: http://www.ncbi.nlm.nih.gov/pmc/articles/PMC2979338/.

Bruce Buckingham et al., "Prevention of Nocturnal Hypoglycemia Using Predictive Alarm Algorithms and Insulin Pump Suspension", "Diabetes Care", 2010, pp. 1013-1017, vol. 33, Publisher: American Diabetes Association, Published in: care.diabetesjournals.org.

Fraser Cameron et al., "Statistical Hypoglycemia Prediction", "Journal of Diabetes Science and Technology", 2008, pp. 612-621, vol. 2, No. 4, Publisher: Diabetes Technology Society, Published in: http://www.ncbi.nlm.nih.gov/pmc/articles/PMC2769757/pdf/dst-02-0612.pdf.

Eda Cengiz et al., "Is an Automatic Pump Suspension Feature Safe for Children with Type 1 Diabetes? An Exploratory Analysis . . . ", "Diabetes Technology & Therapeutics", 2009, pp. 207-210, vol. 11, No. 4, Publisher: Mary Ann Liebert, Inc., Published in: http://www.ncbi.nlm.nih.gov/pmc/articles/PMC2842075/pdf/dia.2008.0102.pdf.

Eyal Dassau et al., "Real-Time Hypoglycemia Prediction Suite Using Continuous Glucose Monitoring", "Diabetes Care", 2010, pp. 1249-1254, vol. 33, No. 6, Publisher: American Diabetes Association, Published in: care.diabetesjournals.org.

Firas H. El-Khatib, et al., "A Bihormonal Closed-Loop Artificial Pancreas for Type 1 Diabetes", "Science Translational Medicine", 2010, pp. 1-12, vol. 2, No. 27, Publisher: American Association for the Advancement of Science, Published in: http://stm.sciencemag.org/content/2/27/27ra27.full.html.

D. Elleri et al., "Suspended insulin infusion during overnight closed-loop glucose control in children and adolescents with Type 1 diabetes", "Diabetic Medicine", 2010, pp. 480-484, vol. 27, Publisher: Diabetes UK, Published in: http://onlinelibrary.wiley.com/doi/10.1111/j.1464-5491.2010.02964.x/.

Roman Hovorka et al., "Manual closed-loop insulin delivery in children and adolescents with type 1 diabetes: a phase 2 randomised crossover tri", "The Lancet", 2010, pp. 743-751, vol. 375, Publisher: Elsevier Ltd., Published in: www.thelancet.com.

Edward Knobbe and Bruce Buckingham, "The Extended Kalman Filter for Continuous Glucose Monitoring", "Diabetes Technology and Therapeutics", 2005, pp. 15-27, vol. 7, No. 1, Publisher: Mary Ann Liebert, Inc., Published in: http://online.liebertpub.com/doi/pdf/10.1089/dia.2005.7.15.

Boris Kovatchev et al., "Multinational Study of Subcutaneous Model-Predictive Closed-Loop Control in Type 1 Diabetes Mellitus: Summary . . . ", "Journal of Diabetes Science and Technology", 2010, pp. 1374-1381, vol. 4, No. 6, Publisher: Diabetes Technology Society, Published in: www.journalofdst.org.

* cited by examiner

KALMAN FILTER BASED ON-OFF SWITCH FOR INSULIN PUMP

CROSS-REFERENCE TO RELATED APPLICATIONS

This application claims benefit of Provisional Appln. 61/762,300, filed Feb. 7, 2013, the entire contents of which are hereby incorporated by reference as if fully set forth herein, under 35 U.S.C. §119(e).

STATEMENT OF GOVERNMENTAL INTEREST

This invention was made with government support under Contract Nos. UL1RR025744 and 5R01DK08559103 awarded by the National Institutes of Health. The government has certain rights in the invention.

BACKGROUND OF THE INVENTION

People with type 1 diabetes must regulate their blood glucose levels each and every day. This means checking their blood glucose levels at least three times per day and correcting their insulin doses as necessary. Errors in delivering too much insulin result in hypoglycemia and the associated sluggishness, coma, and seizures. Delivering too little insulin can result in chronic nerve, heart, and kidney damage. Unfortunately, people with diabetes do not want to pay constant attention to their glucose levels. Alarms are particularly ineffective for low blood glucose levels at night due to the torpor caused by hypoglycemia.

SUMMARY OF THE INVENTION

Applicants recognized a need for a conservative method to mitigate or prevent low blood glucose levels due to too much insulin. Techniques described herein suspend a baseline insulin delivery when low blood glucose levels are predicted; and, thus provides at least an automatic turn off switch for an insulin pump, which switch may be used to warn an operator or actually operate the pump. Various embodiments feed readings from a continuous glucose monitor (CGM) device into a Kalman filter that estimates the value and rate of change of the glucose level. These estimates are used to indicate current or impending low blood glucose levels. Provided that a set of safety rules are satisfied, predictions of low blood glucose result in a suspension of baseline insulin delivery from the insulin pump (called a basal infusion rate). In some embodiments, the suspension continues until the safety rules are no longer satisfied or low blood glucose levels are no longer predicted. The pump is then suitable to be turned on, and such embodiments thus provide at least an automatic turn on switch for an insulin pump that may be used to warn an operator or actually operate the pump. Thus, techniques are provided for a Kalman filter based on-off switch for an insulin pump.

In a first set of embodiments, a computer-readable medium carries instructions that cause an apparatus to determine values for multiple parameters for an automatic on-off switch for an insulin pump configured to inject insulin into a subject. The parameters are selected from a group of parameters including a first prediction time horizon (H1), a first predicted glucose threshold (Goff) for turning the insulin pump off, a maximum shut off time within a first time window, and duration of the first time window. The apparatus is further configured to determine a first safety rule based at least in part on the maximum shut off time (e.g., 120 minutes) within the first time window and the duration of the first time window (e.g., last 150 minutes). The apparatus is also configured to collect a plurality of glucose readings of a glucose level in a bloodstream of a subject up to a current time. The apparatus is also configured to determine an expected current glucose value G and expected current glucose temporal rate of change dG/dt based only on the plurality of glucose readings and a Kalman filter configured for noisy glucose readings of the glucose level in the bloodstream of the subject. The apparatus is further configured to predict a glucose level (Gh1) for a first future time that is the first prediction time horizon (H1) after the current time; and, to issue a command to shut off the insulin pump if it is determined both that the predicted glucose level (Gh1) is less than Goff and that the safety rule is satisfied.

In some embodiments of the first set, the group of parameters also includes a predicted glucose threshold (Gon) for turning the insulin pump on, and a constant basal rate for the insulin pump when the insulin pump is on; and, the apparatus is also configured to issue a command to turn on the insulin pump at the constant basal rate if it is determined both that the predicted glucose level (Gh1) is more than Gon and that the insulin pump is currently turned off.

In some embodiments of the first set, the group of parameters also includes a maximum shut off time within a second time window and a duration of the second time window. In these embodiments, to determine the first safety rule further comprises to determine the first safety rule based at least in part on the maximum shut off time within the second time window (e.g., 180 minutes) and the duration of the second time window (e.g., 8 hours of nightly cycle).

In some embodiments of the first set, the group of parameters also includes a current activity level threshold (Aoff, e.g., acceleration or heart rate) for turning the insulin pump off and a current glucose threshold (Ga, e.g., 180 milligrams per deciliter, mg/dL, 1 mg=$10^{-3}$ gram and 1 dL=$10^{-1}$ liters) for turning the insulin pump off during activity. In these embodiments, the apparatus is further configured to collect a reading of activity level at the current time, and issue a command to shut off the insulin pump if it is determined both that the reading of activity level is more than Aoff and that the expected current glucose value G is less than Ga.

In a second set of embodiments, a computer-readable medium carrying one or more sequences of instructions, wherein execution of the one or more sequences of instructions by one or more processors causes an apparatus to determine values for a plurality of parameters for an automatic on-off switch for an insulin pump configured to inject insulin into a subject. The plurality of parameters are selected from a group of parameters comprising a first prediction time horizon (H1), a first predicted glucose threshold (Goff) for turning the insulin pump off. The apparatus is also configured to collect a plurality of glucose readings of a glucose level in a bloodstream of the subject up to a current time. The apparatus is further configured to determine an expected current glucose value G and expected current glucose temporal rate of change dG/dt based only on the plurality of glucose readings and a Kalman filter configured for noisy glucose readings of the glucose level in the bloodstream of the subject. The apparatus is further configured to predict a glucose level (Gh1) for a first future time that is the first prediction time horizon after the current time; and issue a command to shut off the insulin pump if it is determined that the predicted glucose level (Gh1) is less than Goff.

In other sets of embodiments, a method performs one or more functions of the above computer-readable media or an apparatus is configured to perform those functions.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which.

DETAILED DESCRIPTION

A method and apparatus are described for a Kalman filter based shut-off switch for an insulin pump. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention. In the following various references are cited. The entire contents of each of these references are hereby incorporated by reference as if fully set forth herein, except for terminology that is inconsistent with the terminology used herein.

Some embodiments of the invention are described below in the context of a processor on an insulin pump receiving input from multiple sensors. However, the invention is not limited to this context. In other embodiments a processor on a different device, such as a detached computer or mobile terminal (such as a smart phone) or glucose meter or wearable device, or multiple processors on one or more devices are used, with each performing a part of the overall process.

1. OVERVIEW

A process executing on one or more processors in one or more devices uses recent and current measurements of blood glucose levels in a subject, which measurements are affected by noise and sensor dropout and drift, with a Kalman filter process configured to determine an expected current glucose value G and expected current glucose temporal rate of change dG/dt (called temporal gradient hereinafter) from such data. The G and temporal gradient are used along with a set of one or more safety rules to determine when to shut off or turn on, or both, an insulin pump operating to inject insulin into the subject.

This sections describes some general techniques that can be used in various embodiments. More detailed experimental embodiments are described in the following sections, in which some values for various parameters of the process are determined for particular embodiments.

Figure 1:
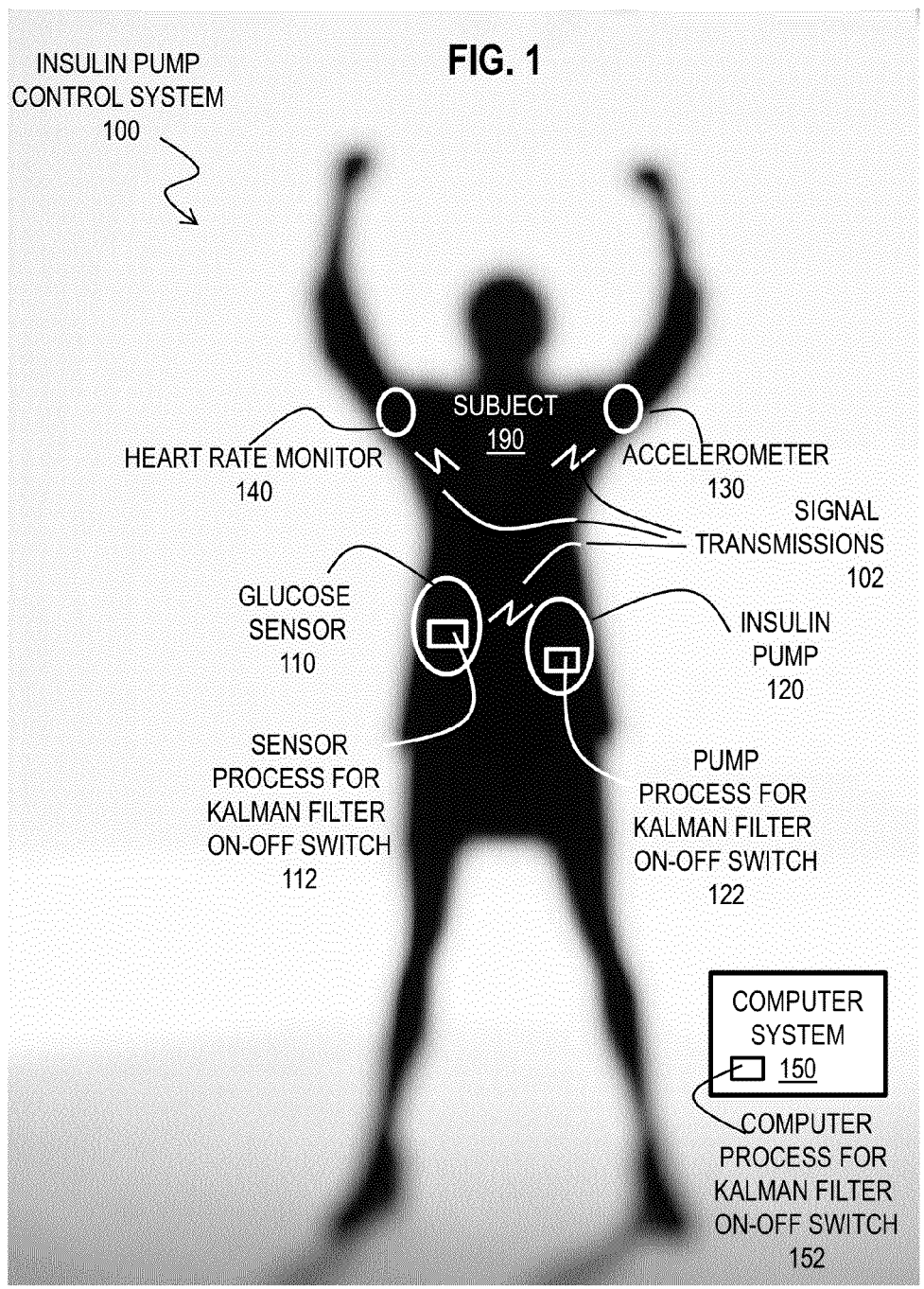
FIG. 1 is a block diagram that illustrates an example insulin pump control system, according to an embodiment.

FIG. 1 is a block diagram that illustrates an example insulin pump control system 100, according to an embodiment. The control system 100 is depicted operating on a subject 190, such as a human test subject or human patient with diabetes; however, the subject 190 is not part of the system 100. The control system 100 includes a glucose sensor 110, insulin pump 120, accelerometer 130, heart rate monitor 140 and computer system 150 (such as the computer system 300 described below with reference to FIG. 7, or chip set 400 described with respect to FIG. 7, or mobile terminal 800, such as a "smart" cell phone, described below with reference to FIG. 8). In other embodiments, one or more of these components are omitted. For example, in some embodiments, a control system includes only a glucose sensor 110 and insulin pump 120. Data is exchanged among these components using one or more signal transmissions 102, which may occur wirelessly or through a hardwired link. Although processes, equipment, and data structures are depicted in FIG. 1 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts. Although components are depicted as positioned at particular locations on the subject 190, in other embodiments one or more of the components are placed in different positions. For example, the accelerometer and heart rate monitor locations are variable. In some embodiments, the heart rate monitor is on a wrist or on a chest strap. In some embodiments, the accelerometer is with the heart rate monitor or on the insulin pump 120 or glucose sensor 110. In some embodiments, it is advantageous to have all components of system 200 integrated into one glucose sensor 110 and one insulin pump 120 which are in wireless communication with each other.

The glucose sensor 110 is configured to obtain measurements of glucose level in the bloodstream of subject 190 (called glucose levels hereinafter) at a series of discrete times and present those measurements to a user of the system 100. Several glucose meters and continuous glucose monitors (CGM) are well known in the art and some are listed in a later section. In the illustrated embodiment, the glucose sensor is configured to transmit a signal, either through a wire or wirelessly, to one or more other components of the system 100. The signal indicates one or more of the measurements of glucose level. The measurements by the sensor 110 are affected by noise, drift and sensor dropouts in which a scheduled measurement does not produce a value of glucose level. In some embodiments, the glucose sensor 110 includes a processor. In some of these embodiments the processor executes one or more steps of a sensor process 112 for the Kalman filter on-off switch process.

The insulin pump 120 is configured to infuse insulin into the body of subject 190 at a series of discrete times. The rate at which insulin is infused is called infusion rate and is expressed in units of volume per unit time. Several insulin pumps are well known in the art and some are listed in a later section. In the illustrated embodiment, the insulin pump is configured infuse at a constant basal infusion rate and to transmit or receive a signal, either through a wire or wirelessly, with one or more other components of the system 100. In some embodiments, the insulin pump 120 includes a processor. In some of these embodiments the processor executes one or more steps of a pump process 122 for Kalman filter on-off switch process.

The accelerometer 130 is configured to obtain measurements of acceleration of a portion of the body of subject 190 (called acceleration measurements hereinafter) at a series of discrete times and present those measurements to a user of the system 100. Several accelerometers are well known in the art and some are listed in a later section. In the illustrated embodiment, the accelerometer 130 is configured to transmit a signal, either through a wire or wirelessly, to one or more other components of the system 100. The signal indicates one or more of the measurements of acceleration. A significant increase in the measured accelerations by accelerometer 130 indicates that the subject 190 may be engaged in some physical activity, such as exercise or recreation. Such activity can affect the measured glucose levels and the consumption of insulin and thus the predicted glucose levels.

Similarly, the heart rate monitor 140 is configured to obtain measurements of heart rate of subject 190 (called heart rate measurements hereinafter, e.g., in beats per minute, bpm) at a series of discrete times and present those measurements to a user of system 100. Several heart rate monitors are well known in the art. In the illustrated embodiment, the heart rate monitor 140 is configured to transmit a signal, either through a wire or wirelessly, to one or more other components of the system 100. The signal indicates one or more of the heart rate measurements. A significant increase in the measured heart rate by heart rate monitor 140 indicates that the subject 190 may be engaged in some physical activity, which, as stated above, can affect the measured glucose levels and the consumption of insulin and thus predicted glucose levels.

Figure 6:
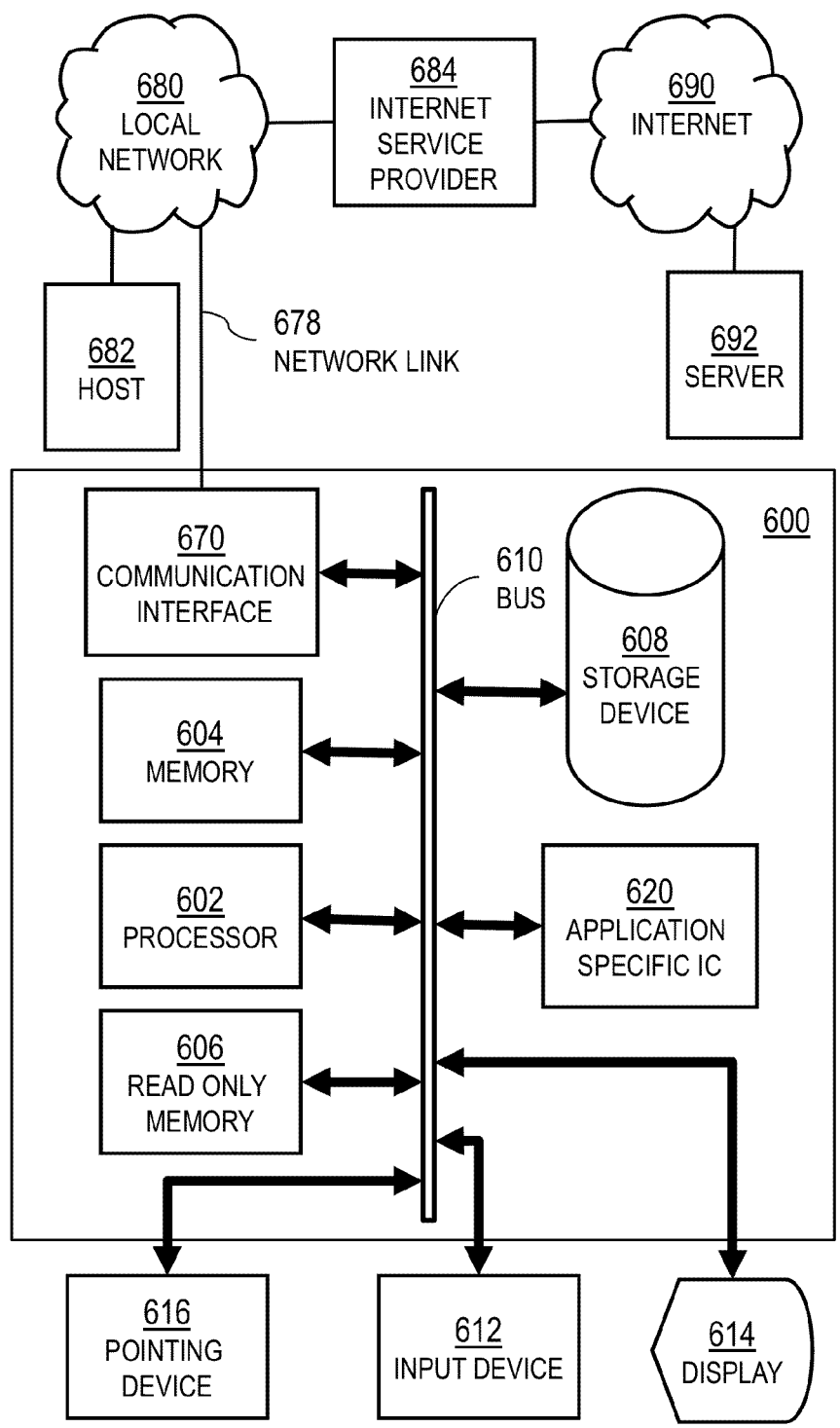
FIG. 6 is a block diagram that illustrates a computer system upon which an embodiment of the invention may be implemented.
Figure 7:
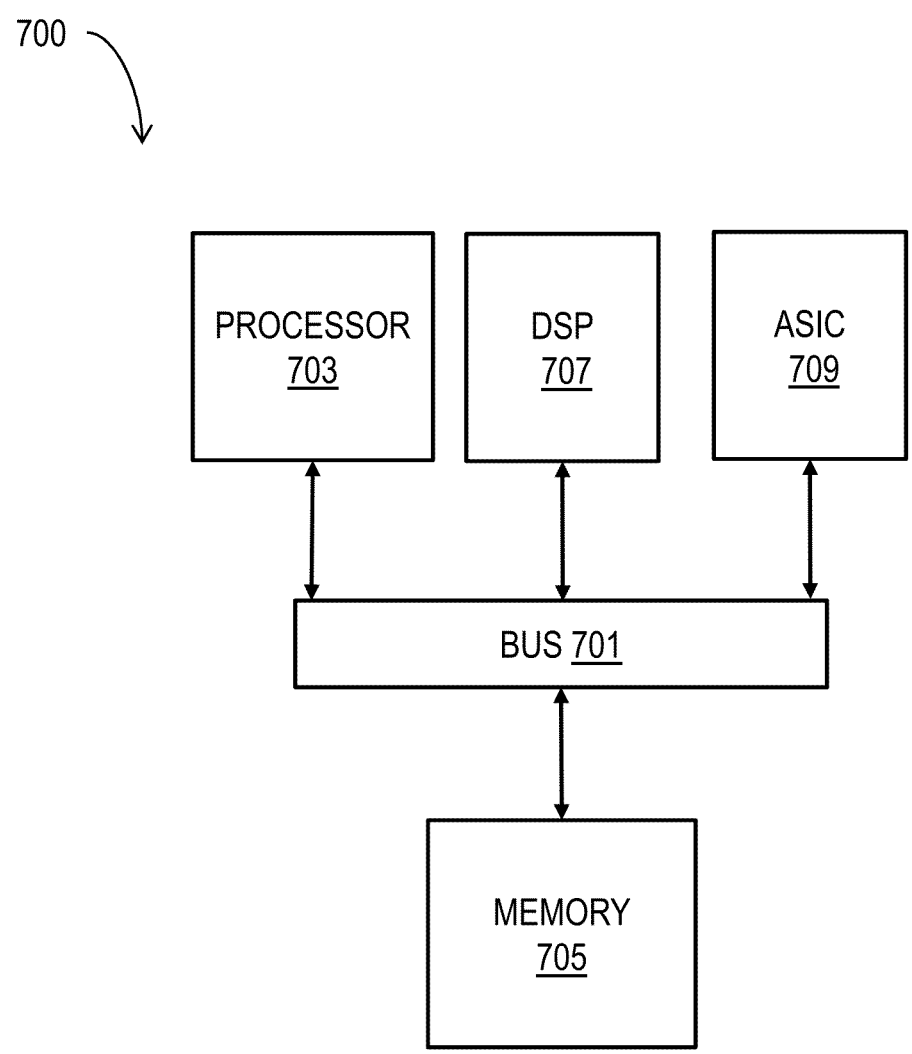
FIG. 7 illustrates a chip set upon which an embodiment of the invention may be implemented.
Figure 8:
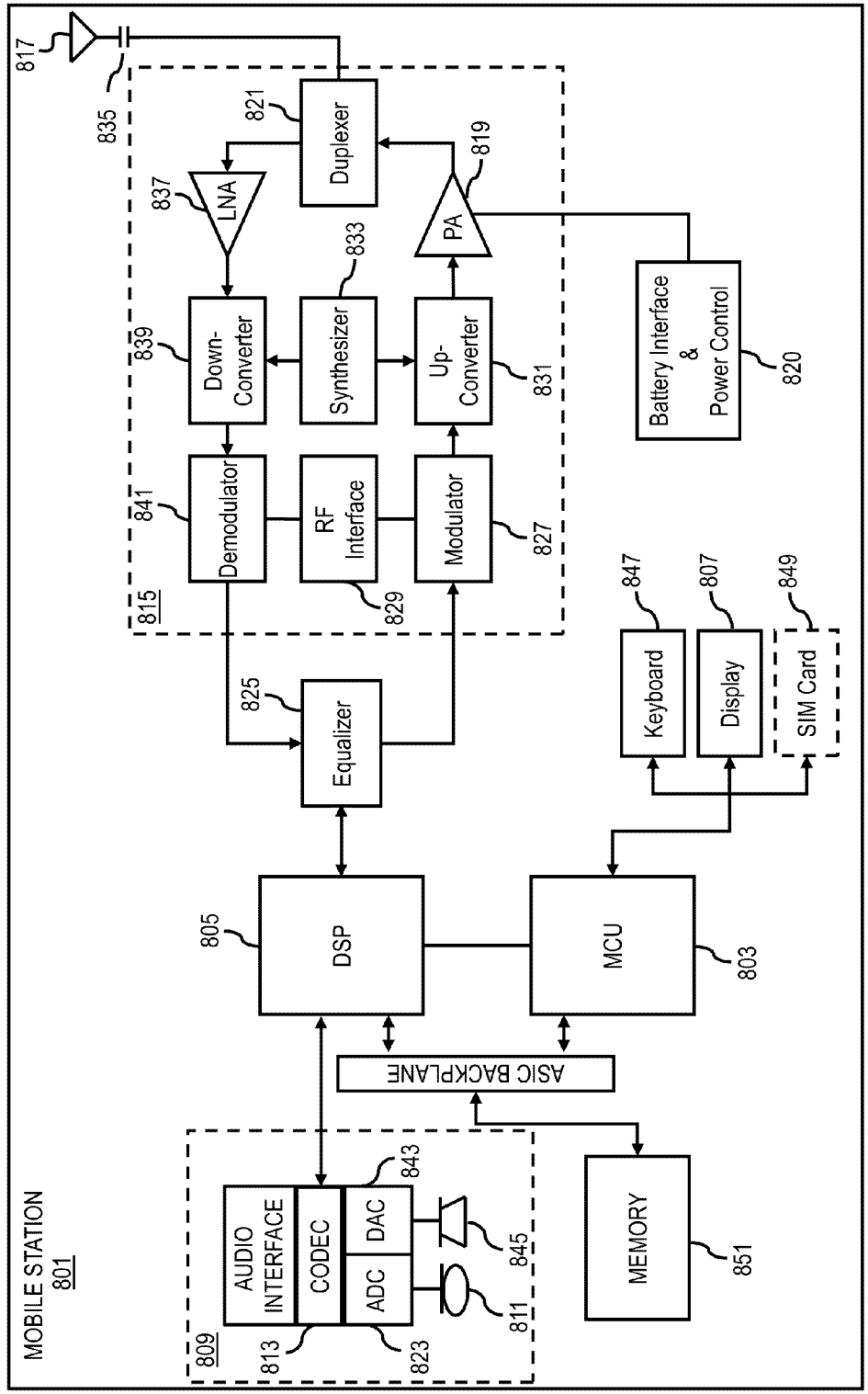
FIG. 8 is a diagram of exemplary components of a mobile terminal (e.g., handset) for communications, which is capable of operating in the system of FIG. 1, according to one embodiment.

Computer system 150, such as the computer system described in more detail below with reference to FIG. 6 or chip set described with reference to FIG. 7 or mobile terminal described with respect to FIG. 8, is configured to receive signal transmissions 102 from one or more other components of system 100 and to perform one or more steps of a computer process 152 for Kalman filter on-off switch process. For example, an embodiment using a computer system 150 is described in more detail in a later section. In some embodiments, data is transmitted to or from computer system 150 over a network to a remote server 692, as depicted in FIG. 6, e.g., in order to provide a remote monitoring function.

Figure 2:
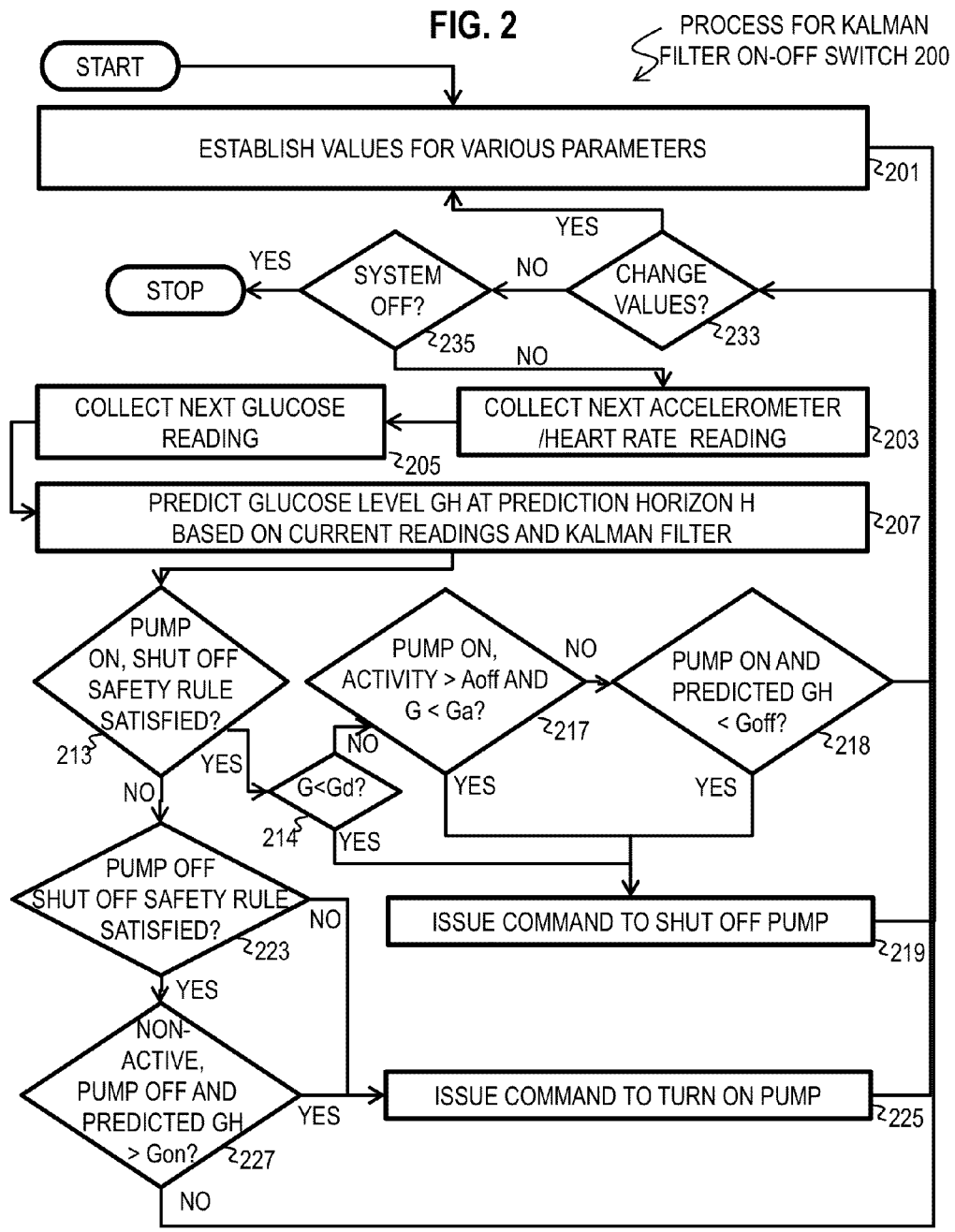
FIG. 2 is a flow chart that illustrates an example process for a Kalman filter based on-off switch for an insulin pump control system, according to an embodiment.

FIG. 2 is a flow chart that illustrates an example process 200 for a Kalman filter based on-off switch for an insulin pump control system, according to an embodiment. In various embodiments, one or more steps of process 200, or portions thereof, are performed by one or more of the sensor process 112, or pump process 122 or computer process 152 depicted in FIG. 1. Although steps are depicted in FIG. 2, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways. For purposes of illustration, the steps of the process 200 are described below as if all steps were performed by a processor on the insulin pump 120, such as pump process 122. In other embodiments, one or more steps or portions thereof are performed by processes on other platforms, such as sensor process 112 or computer process 152 or some combination.

In step 201, values are established for various parameters used by the Kalman filter on-off switch process 200. Various parameters used by the process and values for them based on experimental turning, are described in the next section with reference to specific embodiments. The name of the example parameter of the specific embodiment that corresponds to each parameter of the following list is given in square brackets in the following list.

In various embodiments, the parameters for which values are established during step 201 are one or more parameters selected from a group that includes a first prediction time horizon (H1) [H], a predicted glucose threshold (Goff) for turning the insulin pump off [Goff], a maximum shut off time within a first time window [maxPumpShutOffTimeWithinWindow], and duration of the first time window [maxPumpShutOffTimeWindowSize], a predicted glucose threshold (Gon) for turning the insulin pump on [Gon], and a constant basal rate for the insulin pump when the insulin pump is on, a different second prediction time horizon (H2) [also H], a maximum shut off time within a second time window [maxCumulativePumpShutOffTime], a duration of the second time window [evening], an initial variability of glucose readings [initialBloodGlucoseUncertainty], an initial variability in time rate of change of glucose [initialBloodGlucoseDerivativeUncertainty], a steady state variability of glucose values [steadyStateGlucoseVariance], a default glucose value [initialBloodGlucoseValue], a prior multiplier that determines how fast the defaulting occurs during sensor dropouts [priorMultiplier], a sensor dropout time [MaxSensorTimeSkip], sensitivity of Kalman filter to changes in glucose values (r/q) [r/q], a current activity level (Aoff) for turning the insulin pump off and a current glucose threshold (Ga) for turning the insulin pump off during activity, and a danger current glucose threshold (Gd) for turning off the insulin pump.

In step 233, it is determined whether the value of any of the parameters is to be changed. For example, as a result of the analysis performed on experimental data described in a later section, it is determined to set both the first predicted time horizon H1 and the second predicted time horizon H2 equal to 70 minutes. If so, then control passes back to step 201, described above, to establish values for one or more of the parameters of the process for the Kalman filter based on-off switch 200. If not, control passes to step 235.

In step 235, it is determined whether the system 100 is off. For example, it is determined that the glucose meter 110 or pump 120 or both have been powered down. If so, the process stops. If not, for example, if data is still being received from the glucose monitor 110, and the pump 120 is still powered, then control passes to step 203 or step 205 or both to collect the next readings. In the embodiment of section 3.1, below, the system is off when the test data is exhausted.

In step 203, the next activity reading is collected. As used herein, activity refers to either or both of an accelerometer reading from accelerometer 130 or a heart rate reading from heart rate monitor 140. In other embodiments, other measures of activity are used. In an example embodiment, the activity reading is collected at the insulin pump 120 by recording signal transmissions 102 from either or both of the accelerometer 130 or the heart rate monitor 140. In another embodiment, the activity reading is collected at computer system 150 by recording signal transmissions 102 from either or both of the accelerometer 130 or the heart rate monitor 140. In some embodiments, activity is not measured and step 203 is omitted.

In step 205, the next glucose level reading is collected. In an example embodiment, the glucose level reading is collected at the insulin pump 120 by recording signal transmissions 102 from the glucose monitor 110. In another embodiment, the glucose level reading is collected at computer system 150 by recording signal transmissions 102 from the glucose monitor 110. In some embodiment, the glucose level reading is collected at glucose meter 110 and processed locally by sensor process 112 and the result of that processing (e.g., a Kalman filter output, described below) is sent via signal transmissions 102 to one or more other components of the system. Control then passes to step 207. In some embodiments, step 205 includes dropping suspect or anomalous readings, for example readings indicative of Pressure-Induced Sensor Attenuation (PISA), as described in more detail below as embodiment D, before passing a reading to a Kalman filtering step (e.g., step 207).

In step 207, expected current value of glucose level (G) and expected current value of glucose temporal gradient (dG/dt) are determined based on a Kalman filter configured to process such readings of imperfect measurements. For example, a Kalman filter described in section 2 is performed by computer software instructions that employ values for the following parameters: an initial variability of glucose readings [initialBloodGlucoseUncertainty], an initial variability in time rate of change of glucose [initialBloodGlucoseDerivativeUncertainty], a steady state variability of glucose values [steadyStateGlucoseVariance], a default glucose value [initialBloodGlucoseValue], a prior multiplier that determines how fast defaulting to default values occurs during sensor dropouts [priorMultiplier], a sensor dropout time [MaxSensorTimeSkip] used to determine that the sensor is offline, and sensitivity of Kalman filter to changes in glucose values [r/q]. In the example embodiment, the Kalman filter employs pseudo-readings for missing data. In other embodiments, more or fewer or different parameters, or some combination, are used by the Kalman filter implemented for step 207.

Based on the expected current glucose value G and current temporal gradient produced in step 207 by the Kalman filter, glucose levels are predicted out to one or more prediction time horizons, such as first horizon H1 for falling glucose levels or second prediction time horizon H2 for rising glucose levels, or both. In the example embodiment of subsection 3.1, the first prediction time horizon and the second prediction time horizon are equal. In some embodiments, uncertainty in the expected current value of glucose (G) and expected current temporal gradient are used to determine an uncertainty in the predicted glucose levels. Control then passes to step 213.

In step 213, it is determined whether the shut off safety rules are satisfied when the pump is turned on, e.g., conditions are satisfied for safely shutting off the insulin pump. In various embodiments, the conditions for safely shutting off, or leaving turned off, the insulin pump include one or more of the first four conditions listed in subsection 3.1 or subsection 3.4. The rules depend on values of some of the parameters set during step 201. In other embodiments, one or more other conditions are included in the safety rules. In some embodiments the conditions of the safety rules are applied in priority order from the highest first to the lowest listed last.

In a first illustrated embodiment, condition one is that the pump can only be off for the maximum shut off time (e.g., about 120 minutes) within a first time window (e.g., about 150 minutes) out of every duration of the first time window. If the pump has already been off for the maximum shut off time (e.g., about 120 minutes) within the duration of the first time window (e.g., about 150 minutes), then the safety rule is not satisfied and the pump will be left on (or turned on).

In the first illustrated embodiment, condition two is that the pump can be off the maximum shut off time (e.g., about 180 minutes) within the second time window (e.g., 8 hours overnight) out of every duration of the second time window (e.g., the evening or nightly cycle). If the pump has already been off for the maximum shut off time (e.g., about 180 minutes) within the second time window (e.g., evening cycle), then the safety rule is not satisfied and the pump will be left on (or turned on). This rule seeks to address the risk of a faulty sensor that is consistently reading too low.

In the first illustrated embodiment, condition three is that the pump is not issued a new command if a glucose reading has not been received in the sensor dropout time (e.g., last 20 minutes). This means that no new commands are given until a new glucose reading is received. If a command had previously been given to turn off the pump, then the maximum time the pump would be turned off would be subject to condition one, and the pump will be turned on by condition one even if communication with the glucose sensor 110 is lost indefinitely or permanently.

In the first illustrated embodiment, condition four is that if the current expected glucose level (G) is below the danger current glucose threshold (Gd) parameter value (e.g., 60 mg/dL), then the safety rule to turn off the pump is satisfied and a command is issued to turn the insulin pump off, immediately. This condition is a classic threshold alarm and is represented by step 214 in FIG. 2.

If it is determined in step 213 that the new safety rules (e.g., conditions one, two and three) are satisfied for turning off the pump, and it is determined in step 214 that any conventional condition is satisfied (e.g., condition four, G>Gd), then control passes to step 217. In step 217, it is determined whether to turn off the pump based on activity level of the subject 190, as described in more detail in subsection 3.3 below. For example, it is determined in step 217 whether the insulin pump is currently on, the activity is greater than the value of the parameter Aoff (activity level threshold for turning the insulin pump off), and the current expected glucose value (G) is less than the value of the parameter Ga for turning the insulin pump off during activity and, in some embodiments, that the glucose temporal gradient is negative (glucose level is decreasing). If so, then control passes to step 219, described below, to issue the command to shut off the insulin pump. If not, control passes to step 218. In some embodiments, step 217 is omitted and control passes directly to step 218 from the NO branch of step 214.

In step 218, it is determined whether the insulin pump is currently on and the predicted glucose level at the first predicted time horizon H1 is less than the predicted glucose threshold (Goff) for turning the insulin pump off. If not, control passes back to step 233, described above. If so, control passes to step 219, described next, to issue the command to shut off the insulin pump.

In step 219, a command is issued to shut off the pump. For example, in some embodiments, a message or alarm is sent to a user or operator of the system 100, and the operator turns off the insulin pump at the operator's discretion. In the illustrated embodiment, step 219 is executed by the pump process 122, and actually turns off the insulin pump. In the embodiment described in subsection 3.1, below, the computer process 152 executes step 219 by outputting a data file that indicates the command to shut off the insulin pump for purposes of later analysis and fine tuning of parameter values.

If it is determined, in step 213, that the shut off safety rules are not satisfied while the pump is on, then control passes to step 223. In step 223, it is determined whether the insulin pump is off and the shut off safety rules are satisfied. The safety rules, used alone or in any combination in various embodiments, are described above or in subsection 3.1 or in subsection 3.4. If it is determined in step 223 that the pump is off and the shut off safety rule is not satisfied, then control passes to step 225 to issue the command to turn on the insulin pump. For example, if the pump has been off for 120 minutes out of the last 150 minutes, then step 225 is executed to issue the command to turn the pump back on.

In step 225, a command is issued to turn the insulin pump on. For example in some embodiments, a message or alarm is sent to a user or operator of the system 100, and the operator turns on the insulin pump at the operator's discretion. In the illustrated embodiment, step 225 is executed by the pump process 122, and actually turns on the insulin pump at the value of the parameter for the constant basal rate for the insulin pump when the insulin pump is on. In the embodiment described below in subsection 3.1, the computer process 152 executes step 225 by outputting a data file that indicates the command to turn on the insulin pump for purposes of later analysis and fine tuning of parameter values.

If it is determined in step 223 that the shut off safety rules are satisfied with the pump off, then control passes to 227. For example, if the pump has been off for less than 120 minutes out of the last 150 minutes, then the shut off safety rule is satisfied, it is safe to leave the insulin pump turned off, and control passes to step 227. In step 227, it is determined whether an insulin pump that is shut off should be turned back on. For example, it is determined in step 227 whether the subject is not active, the pump is off and the predicted glucose level at the second prediction time horizon H2 is greater than the value of the parameter Gon (predicted glucose threshold for turning the insulin pump on). If all these conditions are satisfied, then control passes to step 225, described above, to issue the command to turn the pump on.

If it is determined in step 227, that the conditions are not satisfied for turning on the insulin pump based on predicted values of glucose levels at the second prediction time horizon, then control passes to step 233, as described above.

Thus process 200 uses Kalman filter predictions and prioritized safety rules to determine when to suspend or resume basal insulin delivery. The Kalman filter estimates the current value and trend of the blood glucose level over recent time. This can be applied to people with type 1 diabetes who have a continuous glucose monitor and an insulin pump. While people with type 1 diabetes benefit from this algorithm, companies that manufacture the insulin pumps and continuous glucose monitors also benefit. An advantage is that various embodiments are simplifications of voting algorithms that use multiple competing approaches. The resulting process is simple and yet performs significantly better than a simple threshold shutoff and about as well as voting schemes combining multiple methods, as described below. Because as stated above, one or more steps of process 200, or portions thereof, are performed by one or more of the sensor process 112, or pump process 122 or computer process 152 depicted in FIG. 1, therefore, one or more of the processor in glucose sensor 110 or the processor in insulin pump 120 or the processor in computer system 150, which can be the system of FIG. 6 or chip set of FIG. 7 or mobile station of FIG. 8, are the means for determining a first safety rule based at least in part on the maximum shut off time within the first time window and the duration of the first time window; and, with the glucose sensor 110, are the means for collecting a plurality of glucose readings of a glucose level in a bloodstream of a subject up to a current time; and are the means for determining an expected current glucose value G and expected current glucose temporal rate of change dG/dt based only on the plurality of glucose readings and a Kalman filter configured for noisy glucose readings of the glucose level in the bloodstream of the subject; and are the means for predicting a glucose level (Gh1) for a first future time that is the first prediction time horizon after the current time; and, with the insulin pump 120, are the means for issuing a command to shut off the insulin pump if it is determined both that the predicted glucose level (Gh1) is less than Goff and that the safety rule is satisfied; and, with the heart rate monitor 140 or accelerometer 130 or some combination, are the means for determining a current activity level of the subject; and, with the insulin pump 120, are the means for issuing a command to shut off the insulin pump if it is determined both that the current activity level exceeds a threshold value (Aoff), and that a second predicted glucose level (Gha) at a second time horizon (ha) after the current time is less than an glucose activity level threshold (Ga).

2. KALMAN FILTER PRINCIPLES

The principles of Kalman filtering to produce current estimates of values in a noisy data set are described here for the purposes of explanation. However, embodiments of the invention are not limited by the accuracy or comprehensiveness of the description here.

The Kalman filter provides estimates of the current glucose value G and rate-of-change dG/dt at regular (e.g., one minute) intervals using noisy glucose readings obtained less frequently (e.g., every five minutes) and even sporadically. Based on the estimated glucose rate-of-change, dG/dt (also indicated by ΔG for a fixed time interval dt), the Kalman filter also predicts the glucose value at a prediction horizon time H (e.g., 70 minutes into the future).

The Kalman filter uses noisy measurements yk at time steps k to estimate the actual value of an underlying variable xk. For the purposes of the described embodiments, the state of interest x at time step k is a vector with two elements representing the actual glucose value G and the change in glucose ΔG per time step (Δk=1) in a discrete-time model, as defined by Equation 1a, where lower case bold letters represent vectors and upper case bold letters represent matrices $$xk = [Gk, \Delta Gk]^T \quad (1a)$$

where superscript T indicates a vector transpose operation that turns a row vector into a column vector. The measured state yk is based on the continuous glucose monitoring (CGM) reading at time step k $$yk = [GCMk, \Delta CGMk]^T \quad (1b)$$

The Kalman filter also depends on a model of time changes of the state variable. In the illustrated embodiments, the model is linear, e.g., that glucose tends to change at a constant rate for significant periods of time. Note that this assumption also holds for a case of glucose concentration being held relatively constant, which means that the rate-of-change is constant at zero. In the model, the quantity that allows the value of the rate of change variable to adapt is the noise term. More concretely, adding a noise term in the model allows the Kalman filter to adapt the rate of change variable to the new sensor measurements. Without the noise term the estimated certainty for this variable would quickly drop to near zero preventing its adaptation by a noisy sensor measurement. Thus, assuming that the glucose level is driven by its rate of change, that the sensor measures glucose corrupted by noise, and the rate of change is driven by noise, the Kalman filter represents the state by the following Equation 2a and Equation 2b.

$$yk = Cxk + vk \quad (2a)$$

$$x(k + 1) = Axk + wk \quad (2b)$$

where $$A = \begin{vmatrix} 1 & 1 \\ 0 & 1 \end{vmatrix} \quad (3a)$$

$$C = [1 \; 0] \quad (3b)$$

and the vectors wk and vk each represent different independent identically distributed Gaussian noise $$vk = N(0, r) \quad (3c)$$

$$wk = N(0, Q) \quad (3d)$$

$$Q = \begin{vmatrix} 0 & 0 \\ 0 & q \end{vmatrix} \quad (3e)$$

where N indicates a Gaussian distribution with mean 0 and variance r or a matrix Q of variances. Here wk is a 2×1 vector quantity; and, vk is a 1×1 vector quantity (a scalar). Q then is the covariance matrix of a 2×1 vector, and so 2×2. The diagonal terms are the variance of the first and second elements respectively. The non-diagonal terms denote the correlation between the two variables. Here, since only q is nonzero, wk collapses to a scalar Gaussian random variable with variance of $q^{1/2}$. The noise on the glucose estimate is zero, the noise on the ROC of glucose has variance $q^{1/2}$. The ratio of the noise parameters q to r (q/r) is fixed, in the embodiments described below. The absolute value of q is set to ensure that uncertainty on the glucose level is of a reasonable magnitude; for example, q is selected so that the steady state value of the glucose standard deviation is about 10 mg/dL. In other embodiments, other noise models are used. For example, other embodiments use any symmetric positive definite value of Q. Any value would be tuned to provide reasonable accuracy of prediction. A reasonable change would be to increase the top left term to reduce the adaptation of the ROC term, better handling calibrations, but following trends more loosely.

Any linear model that uses glucose information could be used in other embodiments. An easy example is to include a third state reflecting the rate of change of the rate of change of glucose. The noise would then drive that third state. The linear model described by equations 2a and 2b, provide the advantages of simplicity, computational speed, and satisfactory results.

After assuming the model, the Kalman filter estimates the values of xk using the passage of time and the provided CGM time series, yk. These estimates are denoted by x'k and have covariance $\Sigma'k$. This means that the true value xk is normally distributed around the estimate as given by Equation 4a.

$$xk = N(x'k, \Sigma'k) \quad (4a).$$

where N indicates a Gaussian distribution with mean x'k and variance E'k. The state estimate is propagated at each time step as given by Equation 5a.

$$x'k = Ax'(k-1) \quad (5a).$$

The state covariance matrix is also propagated according to Equation 5b when yk values are not available (e.g., at four out of five time steps when k=1 minute and CGM measurements are every five minutes).

$$\Sigma'k = A\Sigma'(k-1)A^T + Q (5b).$$

When a yk value is available (e.g., at every fifth time step), the state estimate is corrected according to Equation 6.

$$x'k = x'k + Lk(yk - Cx'k) \quad (6)$$

and the state covariance matrix is updated according to Equation 7

$$\Sigma'k = \Sigma'k - LkC\Sigma'k (7)$$

where Lk is calculated as given by Equation 8

$$Lk = \Sigma'kC^T\{C\Sigma'kC^T + r\}^{-1} \quad (8)$$

In some embodiments, when measurements are lacking for a time indicated by a parameter (e.g., less than 20 minutes for CGM) that is not considered excessive, then pseudo measurement updates of 140 mg/dL are generated to keep the estimates reasonable, according to Equation 9.

$$x'k = x'k + Lk(140 - Cx'k) \quad (9)$$

In other embodiments, other pseudo measurement values and values for time intervals allowed without measurement are used. For example, in some embodiments the pseudo measurements value 140 is replaced with a value in a range from about above 100 to about less than 180 mg/dl. The state covariance matrix is updated according to Equation 7, but with Lk calculated according to Equation 10.

$$Lk = \Sigma'kC^T\{C\Sigma'kC^T + 1000r\}^{-1} \quad (10)$$

where 1000 is a multiplier that serves to keep the glucose estimate less certain than if actual measurements were available. In other embodiments, other multipliers are used for the variance r. This term determines how fast the estimated glucose values are reset, and how fast the reset estimates adapt to new readings. In other embodiments, other values in a range from about 10 to about 106 are used. The value 1000 has the advantage of working satisfactorily in the example embodiments.

The Kalman filter is initialized with an initial measurement CGM0 and preset values for the uncertainties. For example, in an illustrated embodiment $$x'0 = \begin{vmatrix} CGM0 \\ 0 \end{vmatrix} \quad (11)$$

$$\Sigma'0 = \begin{vmatrix} 3600 & 0 \\ 0 & 1000 \end{vmatrix} \quad (12)$$

In other embodiments, other values for the uncertainties are used. This value is quickly overridden by successive measurement updates and so any positive definite value would work in other embodiments. The above values have the advantage of working satisfactorily together in the example embodiments.

Elements G'k and ΔG'k of the x'k estimate provided by the Kalman filter are used to predict the glucose values out to H time steps into the future using Equation 13.

$$G'(k+H) = G'k + H \Delta G'k \qquad (13)$$

The values used for variables and constants in the above equations are programmed as parameters of the Kalman filter. In some embodiments, certain parameter values are fixed and others are tuned to obtain favorable results for an individual or population of subjects.

TABLE 1

Parameters for the Kalman Filter kept constant in some embodiments.

| Parameter Name | Value | Effect of the Parameter |
|---|---|---|
| initialBloodGlucoseValue | 140 mg/dL | This determines what the estimate defaults to during long sensor dropouts. |
| priorMultiplier | 1000 | This determines how fast the defaulting occurs during sensor dropouts. |
| MaxSensorTimeSkip | 20 min | This sets how long to go without a measurement before determining that it is a sensor dropout. |
| initialBloodGlucoseUncertainty | 36000 (mg/dL)$^2$ | This is the initial estimate for the variance of the glucose. |
| initialBloodGlucoseDerivativeUncertainty | 1000 (mg/dL/min)$^2$ | This is the initial estimate for the variance of the glucose rate of change. |
| maxPumpShutOffTimeWithinWindow | 120 min | This is a constant from safety rule 1, determining the maximum possible duration that the pump can be off at any one time. |
| maxPumpShutOffTimeWindowSize | 150 min | This is the other constant from safety rule 1, determining the window over which a check is made for the pump being on for too long. |
| pumpOffCommandLength | 10 min | The parameter had no observed effect and is not used in example embodiments. |
| maxCumulativePumpShutOffTime | 180 min | This is the constant from safety rule 2, determining the maximum total cumulative off time for an evening. |
| steadyStateGlucoseVariance | 10 mg/dL | This determines an estimated steady state value of the glucose variance. It helps scale the sensor and process noise to reasonable numbers. |

TABLE 2

Parameters for the Kalman Filter tuned in some embodiments.

| Parameter | Nominal | Lower limit | Upper limit | Effect of the Parameter |
|---|---|---|---|---|
| r/q | 1000 | 100 | 10000 | This parameter affects how sensitive the Kalman filter estimates are to the CGM readings, and therefore also the CGM noise. Changing this parameter can make the pump shutoff more or less responsively to short term trends. |
| H | 70 | 50 | 90 | This parameter determines how far the Kalman filter predicts into the future. Increasing it means that the pump will be off for more time before hypoglycemia occurs, but also increases the number of turn offs that will occur where hypoglycemia would not have occurred. |
| Gon | 90 | 90 | 110 | This parameter determines the threshold for predictive turn on. It also bears on how large the sensor bias is expected to possibly be. Raising this is likely to cause more hyperglycemia. |
| Goff | 70 | 70 | 90 | This parameter determines the predictive threshold. It also bears on how large the sensor bias is expected to possibly be. Raising this |

TABLE 2-continued

Parameters for the Kalman Filter tuned in some embodiments.

| Parameter | Nominal | Lower limit | Upper limit | Effect of the Parameter |
|---|---|---|---|---|
| | | | | will provide more pump suspension prior to hypoglycemia. |

3. EXAMPLE EMBODIMENTS

Various experimental embodiments are described in this section. In order to assess the effectiveness of various hypoglycemic prediction and pump shut off algorithms in preventing nocturnal hypoglycemia, a systematic method was developed for inducing nocturnal hypoglycemia. To do this, the basal infusion rate of the subjects was systematically increased with the goal of inducing hypoglycemia (blood glucose <60 mg/dL) by 5 AM on at least 80% of nights. Changes in the pump basal insulin infusion rate were based on a subject's current glucose level and rate-of-change in glucose. The basal rate was not increased more frequently than every 90 minutes. This allowed 60 minutes to determine the full effect of the previous change in basal rate, and then the last 30 minutes (from 60 to 90 minutes) represented the new glucose rate of change. The insulin infusion rate was adjusted; however if the glucose level was <70 mg/dL, then the maximum increase in the glucose infusion rate was limited to 15%.

3.1 Experimental Embodiment A

Several example embodiments running on a computer system 150 rather than on a processor in insulin pump 120, with specific values for various parameters, are described in this subsection.

In this embodiment, a continuous glucose monitoring receiver and insulin pump are housed in the same hardware known as the MEDTRONIC™ MINIMED PARADIGM® REAL-TIME REVEL™ Insulin Pump (model MMT-523 or MMT-723; refer to PMA P980022/S081) of Medtronic, Inc. of Minneapolis, Minn. The MEDTRONIC™ MINILINK™ (model MMT-7703; PMA P980022/S018) serves as the transmitter for the REAL-TIME REVEL™ System. A Comlink (MEDTRONIC™ model MMT-7304, premarket notification K021974) serves as the conduit for communication between the REAL-TIME REVEL™ System and the host computer. The glucose sensor used with the MINILINK™ transmitter in the embodiment is the SOF SENSOR® (MEDTRONIC™ model MMT-7002C; refer to PMA P980022/S012), inserted using the SOF SERTER™ (MEDTRONIC™ model MMT-7510; refer to PMA P980022/S003). The MEDTRONIC™ MINIMED PARADIGM® REAL-Time VEO™ Insulin Pump (MEDTRONIC™ model MMT-554 or MMT-754; refer to IDE G100028) and ENLITE™ Glucose Sensor (MEDTRONIC™ model MMT-7008A) are run in the background for the purpose of passive data collection and are both described in MAF-1787.

CGM blood glucose measurements were calibrated with blood glucose levels measured using the ONETOUCH® ULTRA®2 meter from LifeScan, Inc. of Milpitas, Calif. Blood ketone levels are measured using either the PRECISION XTRA™ meter from Abbott Laboratories of Abbott Park, Ill. or the NOVA 289™ Blood and Ketone meter from NOVA BIOMEDICAL™ Corporation of Waltham, Mass.

In this embodiment of the method, based on a series of CGM sensor glucose readings, appropriate times are determined to suspend an insulin infusion pump in order to reduce the likelihood of hypoglycemia, and appropriate times are also determined to restart the pump in order to minimize post-suspension hyperglycemia.

In the context of this embodiment, all pump suspensions and subsequent restarts are performed manually by study personnel at the recommendation of the method (e.g., method 200). The method includes prioritized rules that are applied every minute. Each rule is described here in the order of priority. The priority means that a rule described first, if it applies, override any later rule if the later rule applies.

1) The pump can be off for a maximum of 120 minutes out of every 150 minutes. If the pump has already been off for 120 of the last 150 minutes then the pump is turned on.

2) The pump can be off for a cumulative maximum of 180 minutes in an evening. If the pump has already been off for 180 minutes then the pump is turned on. This rule seeks to address the risk of a faulty sensor that is consistently reading too low.

3) If a continuous glucose monitoring (CGM) reading is not received in the last 20 minutes then no communication is made with the pump. This means that no new commands are given until a new CGM reading is provided. If a command had previously been given to put the pump on suspend for 120 minutes, then the maximum time the pump suspends insulin delivery would be 120 minutes, even if communication is lost.

4) If the last CGM reading is below 70 mg/dL then the pump is shut off. This is a classic threshold alarm.

5) If the pump is on and a Kalman filter predicts that the glucose level will be below a threshold (nominally 80 mg/dL) at some minutes (nominally 70 min) from the current time, then the pump is turned off.

6) If the pump is off and a Kalman filter predicts that the glucose level will be above another threshold Gon (nominally 100 mg/dL) at some minutes (nominally 70 min) from the current time, then the pump is turned on.

To prevent sensor dropouts from violating the safety constraints in rules 1 and 2, the pump is also turned off using a timed suspension command. The duration of suspension is set to the maximum time allowed by rules 1 and 2. This way, in the absence of any communication the pump adheres to the safety constraints.

In some embodiments a tunable parameter is used for the total duration of pump suspension. A maximum cumulative suspension time limit, Tscmax, to cap the suspension time for a single night is introduced. Initially this parameter is set to 180 minutes. This value can then be modified in other embodiments. In addition, if the pump has been turned off for more than 120 minutes in a 150-minute window, the pump would be restarted at the usual basal rate for ½ hour before additional suspensions are allowed. Previous embodiments obtained data using 1 minute sensor readings. In the illustrated embodiments, the Kalman filter is used to change from 1 minute readings to 5 minute readings (e.g., from a FREESTYLE NAVIGATOR® sensor from Abbott Diabetes Care, Inc. of Alameda, Calif. to the SOF™ sensor). The performance of the Kalman predictive alarm was therefore assessed against previous data sets in predicting the initial hypoglycemic event in overnight studies. The Kalman performance was in a range that was comparable to the previous, best performing 5-vote system. It was therefore decided to move forward with embodiments using this one embodiment to simplify the code and allow for a more rapid transition to using an embodiment that might be programmed into a patient's sensor augmented insulin infusion pump.

An example Communication Interface Module is responsible for communicating with the CGM-pump Module to obtain continuous glucose monitoring (CGM) values and then communicating the CGM values to the Control Algorithm Module. After the Control Algorithm Module processes the CGM values, the Communication Interface Module relays commands to the REVEL™ pump to turn the pump off and on based on the recommendations of the Control Algorithm Module, previous CGM values and time. CGM glucose and prescribed insulin dose changes are logged by the Communication Interface Module.

An example CGM-pump Module consists of a dynamic link library (DLL), purpose-built by MEDTRONIC™ engineers for inclusion in this experimental embodiment, that exposes a small subset of functions available on the CGM and infusion pump. Normally, these functions are accessed interactively using the REVEL™ hardware, but in this embodiment the functions is accessed automatically by control software.

Both the Communication Interface Module and the Control Algorithm Module read in multiple parameters' values stored in a configuration file (e.g., a text file) located at a standardized path on each processor. These parameters control how the Control Algorithm software module and Communications Interface software module behave. Prior to an inpatient admission visit, clinic personnel or other operators download a subject-specific version of the configuration file, e.g., using an interface on a Web site for the system, save it on the local processor for the subject, and perform a test run of the study software to confirm that the configuration file is being read properly by the local process. In some embodiments, the configuration file is encrypted during the download process so that the configuration file is not readable by unauthorized personnel or equipment.

Tables 3 indicates how altering the tunable parameters of Table 2 to their extreme values for various embodiments changes 1) the average suspension time before hypoglycemia from a data set where hypoglycemia was forced and 2) the average amount of time that the pump spends suspended for a data set where another suspension algorithm was tested. In each embodiment, only one parameter was changed to its extreme value. The average amount of time spent with the pump suspended using the nominal tuning is 118 minutes out of the total possible pump suspension duration of 180 minutes.

TABLE 3

Performances based on value changes to some tunable parameters.

| Parameter Change | Average delay in pump suspension preceding hypoglycemia (min) | Average increase in total suspension time (min) |
|---|---|---|
| Goff = 70 | 3 | −29 |
| Goff = 90 | −3 | 18 |
| Gon = 110 | 0 | −2 |
| Gon = 90 | 0 | −20 |

TABLE 3-continued

Performances based on value changes to some tunable parameters.

| Parameter Change | Average delay in pump suspension preceding hypoglycemia (min) | Average increase in total suspension time (min) |
|---|---|---|
| H = 90 | −6 | 15 |
| H = 50 | 7 | 26 |
| r/q = 10000 | 8 | −12 |
| r/q = 100 | −1 | 0 |

In-silico validation has been performed to show that this proposed algorithm using 5-minute CGM data performs as intended, showing that it 1) recommends pump suspension sufficiently far in advance of actual hypoglycemia, 2) produces results comparable to those of prior prediction algorithm that used CGM readings every minute, and 3) obeys the defined safety constraints. This validation involves retrospective application of the proposed algorithm to two previously obtained sets of clinical data. The first data set was obtained when basal rates were gradually increased to induce hypoglycemia. The second data set also used elevated basal rates to induce hypoglycemia, but used a hypoglycemia prediction algorithm to suspend the insulin pump in an effort to prevent hypoglycemia.

Figure 3A:
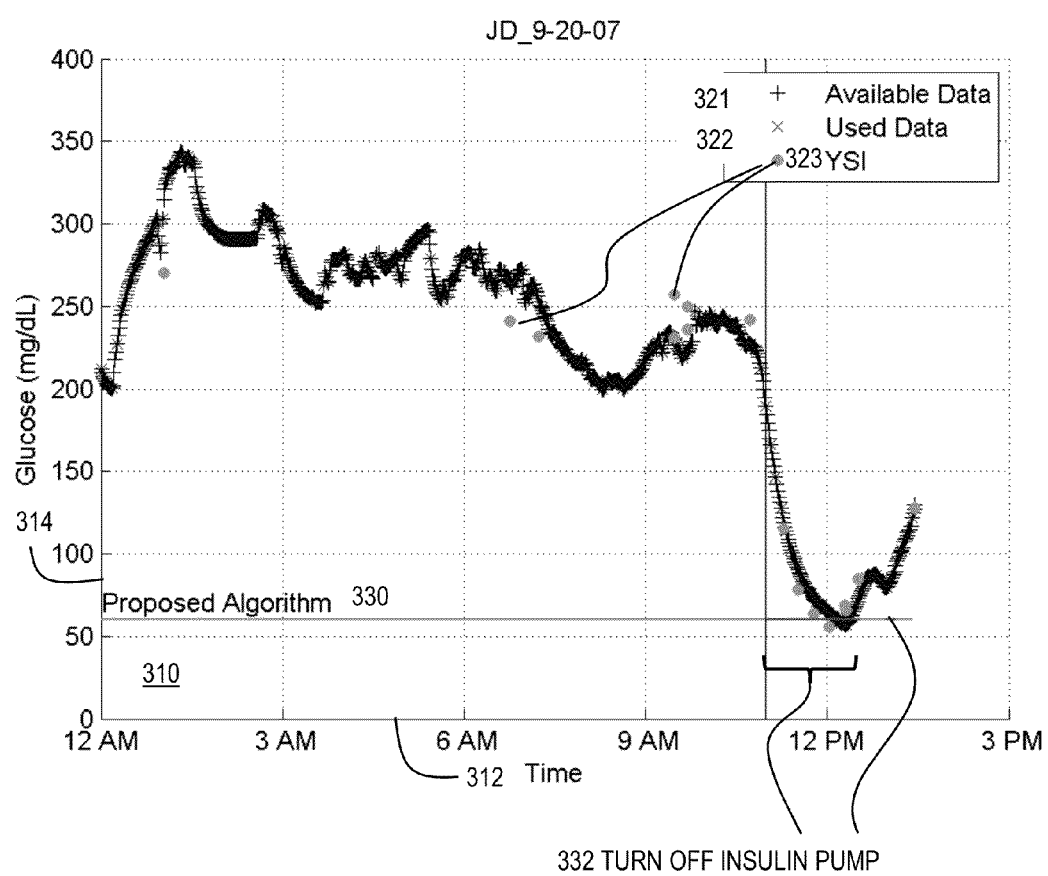
FIG. 3A to FIG. 3C are plot that illustrate example comparison of CGM time series with periods during which a pump should be turned off, according to an embodiment.
Figure 3B:
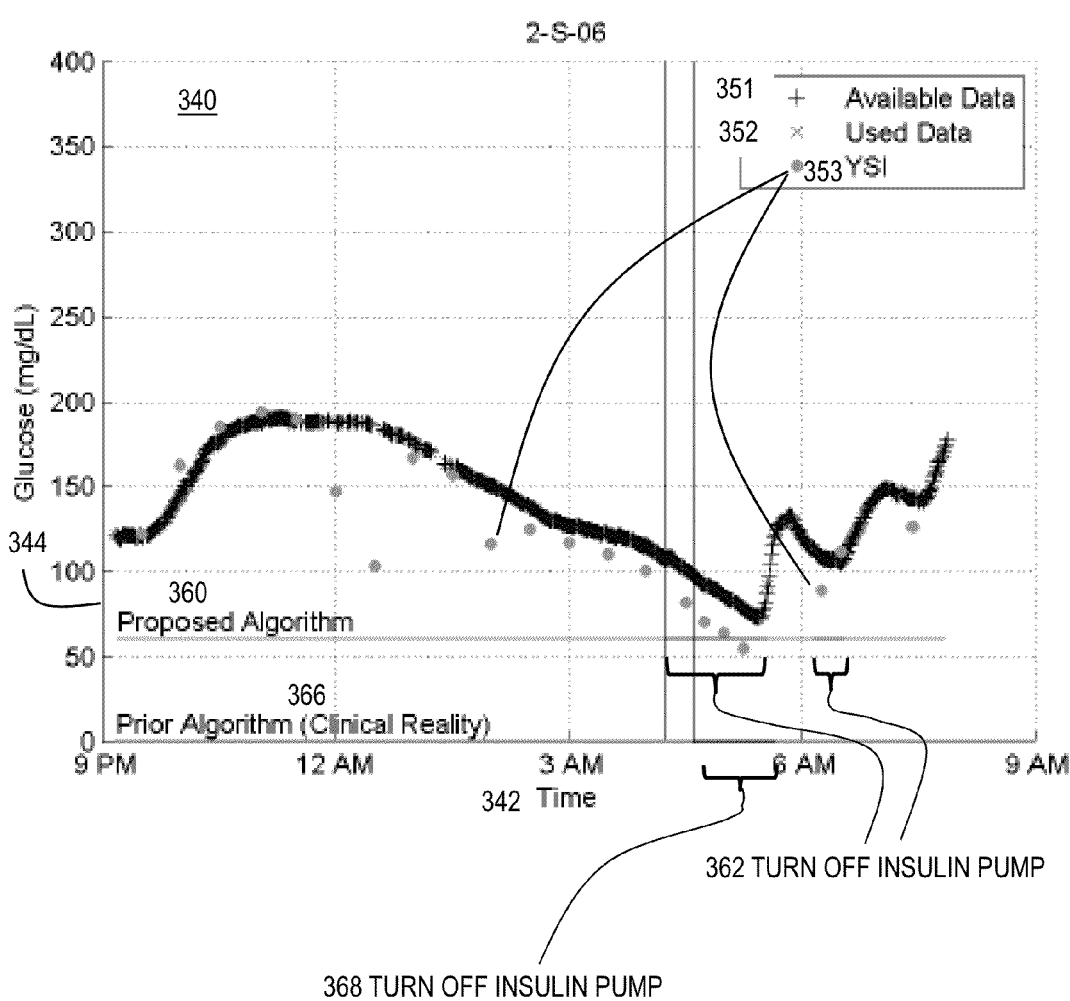

In the first set of example embodiments, to assess the amount of time that insulin delivery would be suspended prior to a hypoglycemic event, the algorithm was assessed on a clinical data set in which hypoglycemia was induced by gradually increasing basal infusion rates. The duration of suspension before hypoglycemia occurred is an approximation of whether hypoglycemia would have been prevented. CGM measurements were checked using a YSI LIFE SCIENCES™ glucose meter from XYLEM™ of White Plains, N.Y. and labeled in the Figures as YSI. Hypoglycemia was confirmed by a single YSI reading less than 60 mg/dL. Plots for representative cases are shown in FIG. 3A and FIG. 3B. FIG. 3A is a plot 310 that illustrates an example comparison of CGM time series with periods during which a pump should be turned off, according to an embodiment. Horizontal axis 312 indicates time in hours and vertical axis 314 indicates glucose level in mg/dL. The 1 minute data is plotted as plus signs 321 and the 5 minute data used in the method is indicated by x signs 322. YSI glucose meter measurements are marked as solid circles 323. The hypoglycemia line 330 at 60 mg/dL indicates when the method 200 would turn the insulin pump off 332, otherwise the insulin pump is left or turned on. The reasonable amount of time for pump suspension is defined based on the YSI readings to be the time between the first YSI value less than 60 mg/dL and the previous peak YSI value. FIG. 3A is an example of how limited the available suspension time can be. Until about 11 AM it is totally unreasonable to predict the hypoglycemia that occurs at 12 PM, giving a maximum of 60 minutes to suspend the pump. In this case out of a possible 139 minutes of suspension since the last YSI glucose peak (at about 10 AM), the algorithm suspended for 40 minutes (starting at about 11:30 AM).

Figure 3C:
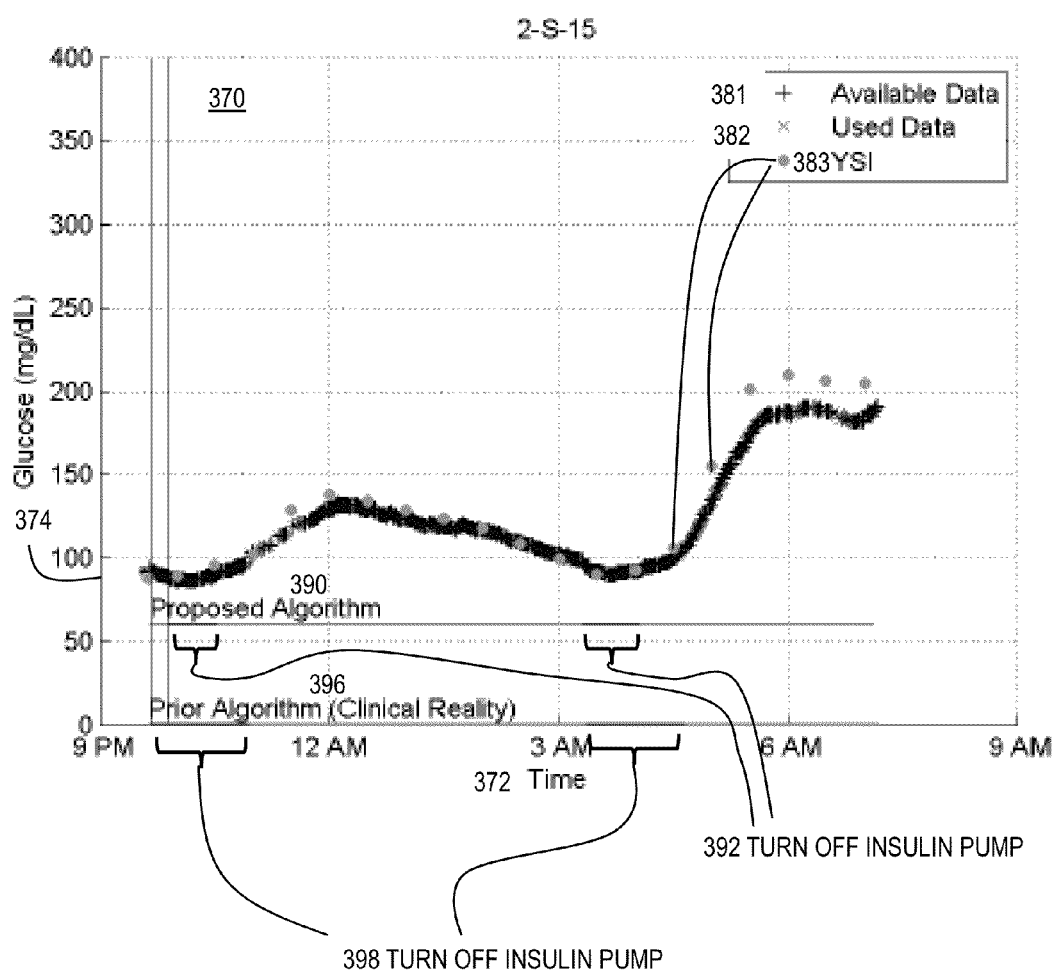

Similarly, FIG. 3B is a plot 340 that illustrates an example comparison of CGM time series with periods during which a pump should be turned off, according to an embodiment. Horizontal axis 342 indicates time in hours and vertical axis 344 indicates glucose level in mg/dL. The 1 minute data is plotted as plus signs 351 and the 5 minute data used in the method is indicated by x signs 352. YSI glucose meter measurements are marked as solid circles 353. The hypoglycemia line 360 at 60 mg/dL indicates when the example embodiment would turn the insulin pump off 362, otherwise the insulin pump is left or turned on. For comparisons described below, the offset line 366 at 0 mg/dL indicates when the previous approach using 5 votes would turn off the insulin pump 368. FIG. 3C is a plot 370 that illustrates an example comparison of CGM time series with periods during which a pump should be turned off, according to an embodiment. Horizontal axis 372 indicates time in hours and vertical axis 374 indicates glucose level in mg/dL. The 1 minute data is plotted as plus signs 381 and the 5 minute data used in the method is indicated by x signs 382. YSI glucose meter measurements are marked as solid circles 383. The hypoglycemia line 390 at 60 mg/dL indicates when the example embodiment would turn the insulin pump off 392, otherwise the insulin pump is left or turned on. For comparisons described below, the offset line 396 at 0 mg/dL indicates when the previous 5-vote algorithm would turn the insulin pump off 398.

Figure 4:
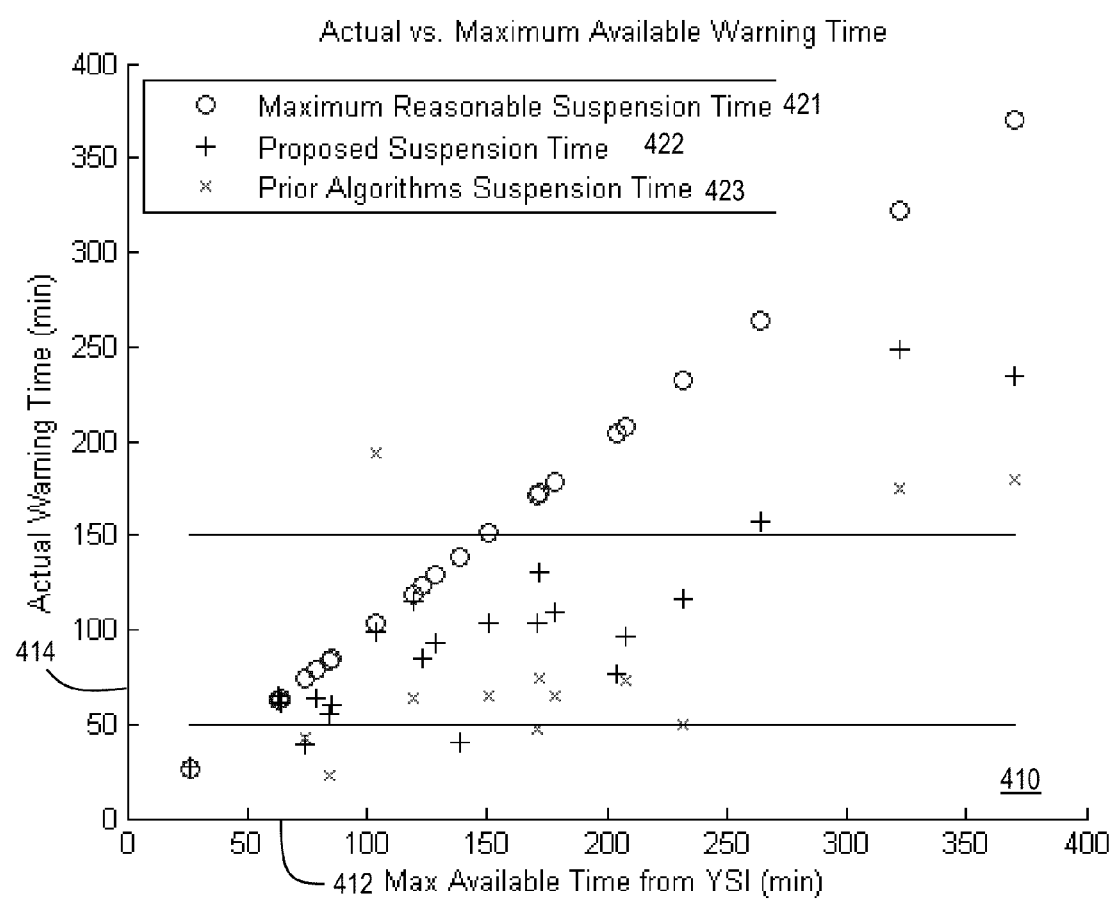
FIG. 4 is a plot that illustrates an example amount of time available for reasonable pump suspension, according to an embodiment.

FIG. 4 is a plot 410 that illustrates an example amount of time available for reasonable pump suspension, according to an embodiment. The horizontal axis 412 indicates the maximum available time between the first YSI value less than 60 mg/dL (confirmed hypoglycemia) and the previous YSI peak value, in minutes. The vertical axis 414 indicates the warning time in minutes given by various methods, also in minutes. The open circles 421 indicating a maximum reasonable suspension time equals the maximum available time and lies along the line through the origin with slope 1. The plus signs 422 indicate the time before the hypoglycemia confirming YSI value that the pump would have suspended for the example embodiment of the method 200. The x's 423 are the turn off times for a previous, 5-vote algorithm. This plot 410 shows that the example embodiment both provides a high proportion of the available suspension time, and generally more (earlier) suspension time than the previous 5-vote algorithm did. This additional time may lead to a drop in the 25% failure rate of the previous 5-vote algorithm.

From FIG. 4, it is observed, that when the amount of reasonable suspension time is short, then the example embodiment uses a majority of the reasonable suspension time. When there is more reasonable suspension time available, then the example embodiment levels off the actual suspension time at about 150 minutes. The overall mean amount of suspension time is 100 minutes. This corresponds to 66% of the reasonable suspension time, or 84% of the reasonable suspension time saturated at 150 minutes. In 19 of the 22 cases examined, the example embodiment would have suspended the pump for more than 50 minutes before actual hypoglycemia. In three cases where the pump provided 28, 39, and 40 minutes of pump suspension, all less than 50 minutes of warning, the lack of warning was caused by an accelerating rate of decline and a sensor bias of 24 mg/dL, a rapidly accelerating rate of decline following a sharp rise, and an accelerating rate of decline with a sensor bias of 34 mg/dL, respectively. These circumstances violate the general expectation for both a positive sensor bias of 20 mg/dL or less, and a steady, or decreasing rate of glucose decline. In general, FIG. 4 shows that the example embodiment makes good use of the available time to suspend the pump.

The performance of the example embodiment is here compared to the clinical performance of the previous 5-vote pump suspension algorithm, which used a voting scheme to combine five individual algorithms, and was based on better one-minute data. The 5-vote data is from a clinical test and so the pump suspension shown for the prior algorithm is a real pump suspension and affects the glucose levels. An example of this result is shown above in FIG. 3B. This plot 340 shows when the pump was suspended 368 based on the previous 5-vote algorithms as well as the timing of suspensions 362 from the example embodiment. Since the example embodiment uses CGM readings only every 5 minutes instead of every minute, all of the CGM readings (pluses) and the subset that is used by the proposed algorithm (x s) are also shown, as described above. Also as described, the plot shows the YSI readings (solid circles) and the pump suspension times 368 and 362 for the previous 5-vote algorithm and example embodiment, respectively.

The different time series for 19 cases are divided into three categories: 1) cases where the YSI readings went below 60 mg/dL requiring intervention (failures of the previous 5-vote algorithm); 2) overly-aggressive pump suspension cases where the YSI readings exceeded 150 mg/dL after pump suspension by the 5-vote algorithm; and 3) cases where the previous 5-vote algorithm performed appropriately (nominal cases).

There were 4 failure cases out of 16 where the YSI values dropped below 60 mg/dL, and an additional 4 near failures where the YSI value dropped below 70 mg/dL. To indicate improvement in performance, it is shown that the example embodiment would have suspended the pump earlier in most cases, thereby increasing the chances that the failure or near failure would have been averted. For the four failure cases the example embodiment would have suspended the pump 10, 23, 83, and 5 minutes earlier, respectively (an average of 30 minutes earlier). For the four near failure cases the example embodiment would have suspended the pump 48, 37, −25, and 0 minutes earlier respectively (bringing the average of the 8 cases to 23 minute earlier).

Out of the 12 cases where hypoglycemia did not occur, 4 had YSI values above 150 mg/dL. A suspension to prevent hypoglycemia should not cause high blood glucose values (hyperglycemia). The pump suspension should cease after the hypoglycemia has been prevented, allowing the resumption of the basal insulin rate to prevent subsequent hyperglycemia. Here improvement is approximated by the amount of time that the pump spent suspended. Less time spent with the pump suspended should induce lower peak glucose levels following suspension. For the 4 cases with YSI values greater than 150 mg/dL (YSI peak values of 261, 170, 180, and 210 mg/dL) the example embodiment triggered a pump shut off for 104, 122, 55, and 71 minutes less (respectively). The pump suspensions for one case are shown in above in FIG. 3C. Here both the previous 5-vote algorithm and the example embodiment suspended the pump twice, with both times the suspensions at intervals 398 of the previous 5-vote algorithm lasting longer than the corresponding example embodiment suspension intervals 392. The mean reduction in total pump suspension time over the four cases was 88 minutes, showing improvement by the example embodiment.

Subtracting the hypoglycemic, near hypoglycemic and overly aggressive cases leaves 5 nominal cases. For these cases the example embodiment suspends and resumes the basal rate at approximately the same times as the previous 5-vote algorithm. This demonstrates safety, because the previous 5-vote algorithm was previously found safe. The example embodiment suspended the pump within 5 minutes of the previous voting scheme with two exceptions. In the first exception, the example embodiment triggered a 27 minute pump suspension based on a temporary increase in the rate of decline in the sensor signal. In the second exception, the previous voting scheme triggered a pump suspension at a YSI value of 142 mg/dL that was probably not necessary, where the example embodiment did not trigger a pump suspension.

The timing of the pump restart was also compared using the example embodiment compared to the previous voting for the 5 algorithms. In two cases, the example embodiment suspends the pump for 105 and 32 minutes less and in these cases the YSI readings crested 135 mg/dL in the clinical study. By suspending the pump for less time, the peak glucose levels should drop for the example embodiment. In another two cases, the example embodiment suspends the pump 38 and 55 minutes less, when the observed YSI value in the clinical study increased to 106 and 116 mg/dL respectively. This reduction in the pump suspension time would lower the peak glucose values and likely result in more pump suspension due to the decreased glucose values. In the last case, the example embodiment suspends 29 minutes longer when the peak YSI glucose post suspension in the clinical study increased to 145 mg/dL. This difference in total suspension time is likely to increase hyperglycemia.

Validation also included checks to confirm that the code as written enforced the safety constraints. This led to 4 tests to test safety constraints 1-4. Running the algorithm for the 16 patients, there were no violations of the safety constraints.

3.2 Embodiment B

More recent embodiments and experimental results are described in this subsection. In this embodiment, H is 70 minutes but Goff is 80 mg/dL rather than nominal 70 mg/dL and Gon is 100 mg/dL rather than nominal 90 mg/dL.

The experiments conducted used either or both the ENLITE™ CGM or the SOF CGM and were compared to the CGM values fed to the algorithm, denoted "Algo CGM." The triangles at the top are the suspension cues from this algorithm. The experimental protocol included: 7 PM admission (dinner at 6 PM); systematic increase in basal insulin at 9 PM (to induce hypoglycemia); continued observations until 7-8 AM; subjects remain in recumbent position; reference glucose taken every 15-30 min (including either or both a YSI measurement or a measurement from a GLUCOSCOUT® sensor available from INTERNATIONAL BIOMEDICAL™ of Austin, Tex.); blood ketone measurements at study onset and again after suspension, before breakfast at 8 AM. The GLUCOSCOUT® is a reference blood glucose meter. It is slightly less of a gold standard than the YSI (yellow springs instruments) meter, but more automatic.

This embodiment prevented hypoglycemia in 12 of 16 subjects. One of the failures was due to a CGM sensor that was consistently reading 58 mg/dL above the actual blood glucose (e.g., from YSI or GlucoScout). The average glucose at start of suspension was 112 mg/dL; the average glucose at end of suspension was 106 mg/dL; and the average glucose at morning termination was 137 mg/dL. All these blood glucose levels are in a range considered well controlled.

3.3 Embodiment C with Activity Level

This subsection describes some embodiments of method 200 that include steps 203 and 217 to monitor and utilize activity level. For convenience, these embodiments are called method 200 with step 217.

Regular aerobic exercise is considered an essential component of the management of type 1 diabetes (T1D). However, exercise-associated hypoglycemia is a frequently reported adverse event and can occur during exercise or several hours afterwards. Although pre-meal dose reduction of exogenous insulin or increasing carbohydrate intake can be effective at decreasing the incidence of exercise-associated hypoglycemia, people with T1D often do not perform such adjustments. Suspension of an insulin pump at the beginning of moderate aerobic exercise has been shown to reduce the risk of exercise-associated hypoglycemia, albeit with an increased risk of hyperglycemia. Algorithm-based pump suspension offers a more nuanced, user-independent means for reducing insulin delivery, with the potential to avoid hypoglycemia and remain euglycemic (well controlled). However, although previously used pump suspension algorithms based on continuous glucose monitor (CGM) trends can reduce hypoglycemia in a sedentary setting, none of these prior algorithms have been successfully applied to exercise.

In the embodiment described in this section, activity data derived from the use of a accelerometer or heart rate monitor (HRM) device, or some combination, is incorporated into the method (e.g., as step 217). An illustrated embodiment of the augmented algorithm using both activity sensors is tested on a simulator based on outpatient monitoring data.

To be eligible for the study, each subject had to 1) be between 10 and 60 years of age, 2) have a clinical diagnosis of type 1 diabetes for >12 months, 3) use a downloadable smart insulin pump (with programmable carbohydrate to insulin ratios, correction doses, and insulin on board features) for insulin delivery, 4) own a CGM or agree to wear a loaned CGM (with appropriate teaching, as needed) for purposes of study participation.

Subjects had an initial visit with a study investigator for a baseline medical history and physical exam, then underwent placement of the ZEPHYR BIOHARNESS™ 3 (Zephyr Technology, Annapolis, Md.) combined accelerometer/hear rate monitor (HRM), which is encased in a chest strap that is worn directly on the skin. If not already in use, a DEXCOM™ G4 Platinum CGM (Dexcom Inc., San Diego, Calif.) or MEDTRONIC REVEL CGM (Medtronic Inc., Minneapolis, Minn.) was placed and appropriate teaching provided. Subjects were instructed to wear the accelerometer/HRM, as well as the CGM and insulin pump on a continuous basis as they went about their everyday activities, with the exception of water-based activities (re-charging of the accelerometer/HRM was also required every 36 hours and was recommended to be done overnight). Specific instructions were given for subjects to not deviate from their usual lifestyle or diabetes management strategies during the monitoring period. Subjects were also asked to record the type, duration, and intensity of any exercise lasting >20 minutes on an activity log. After the completion of the monitoring period, each subject's insulin pump, CGM, and accelerometer/HRM were downloaded for analysis. When available, activity logs were also obtained and incorporated in the analysis.

The Kalman filter was used with a either a 30 minute or 70 minute prediction horizon H, in different sets of embodiments. In both sets of embodiments, a blood glucose threshold, Goff, of 80 mg/dl for pump suspension, a safety feature (e.g., Rule 6) is in place to prevent suspensions when the CGM readings are increasing.

The illustrated embodiment suspends the pump when activity levels exceeded predefined thresholds, for example, 0.1 vector magnitude units (VMU) on the accelerometer, or 90 beats per minute (bpm) on the heart rate monitor or some combination, and the glucose value is both decreasing and currently below a threshold Ga of 180 mg/dL.

These illustrated embodiments were tested by simulation. The simulator uses glucose and insulin data from subjects and then removes the effect of insulin given when a suspension is commanded. Daytime data between 6 A.M. and midnight was analyzed and events beneath a blood glucose threshold of 70 mg/dl were defined as hypoglycemic. The simulator compared the number of hypoglycemic events among four different versions of the data: the first version is the real-life data without any algorithmic interventions; the second version simulates the use of the method 200 without step 217; the third and fourth versions use the illustrated method 200 with step 217 informed with heart rate alone or acceleration data alone, respectively, In the simulation, it was assumed that the insulin used in the real-life setting acted according to 1) the patient's insulin sensitivity calculated empirically using the data and the 1800 rule, and 2) an insulin time action profile taken as the average of aspart and lispro curves published by Frohnhauer, Swan. When the illustrated embodiment issued a pump suspension command, five minutes of the real-life basal rate was removed per the assumed time-action profile and the subsequent effect to future glucose levels was then computed. As the simulator works optimally for small changes in the glucose levels, drastic fluctuations in blood glucose were avoided by resetting the effects of previous commanded suspensions when the glucose level was above 100 mg/dL and the actual data contained no hypoglycemic readings in the following three hours.

Mean age of participants was 22.2 years (range 10.7-45.5) and mean reported hemoglobin A1c was 7.6% (range 5.9-10.3%). The mean length of monitoring was 4.9 days (range 1-16). Data was not collected on subject #4 because of extremely thin body habitus (physique), which resulted in an inability to keep the accelerometer/HRM on the chest. No adverse events were reported related to the wearing of any study devices. A total of 11,061 CGM readings were recorded during the monitoring period. The comparison of hypoglycemic events between the four intervention groups is shown in Table 4.

TABLE 4

Performances of different embodiments.

| Embodiment | # readings below 70 mg/dL |
|---|---|
| None (actual real-life performance without method 200) | 336 |
| Method 200 without step 217 | 121 |
| Method 200 with step 217 based on heart rate monitor (HRM) | 90 |
| Method 200 with step 217 based on accelerometer | 81 |

The embodiment without step 217 resulted in a 64% reduction in hypoglycemia. The embodiment with step 217 based on HRM provided a 73% reduction. The embodiment with step 217 based on the accelerometer provided a 76% reduction. There were some minutes of suspension per minute of hypoglycemia reduction. On no occasions did any embodiment fail to suspend before the subject became hypoglycemic in the real-life setting.

Figure 5A:
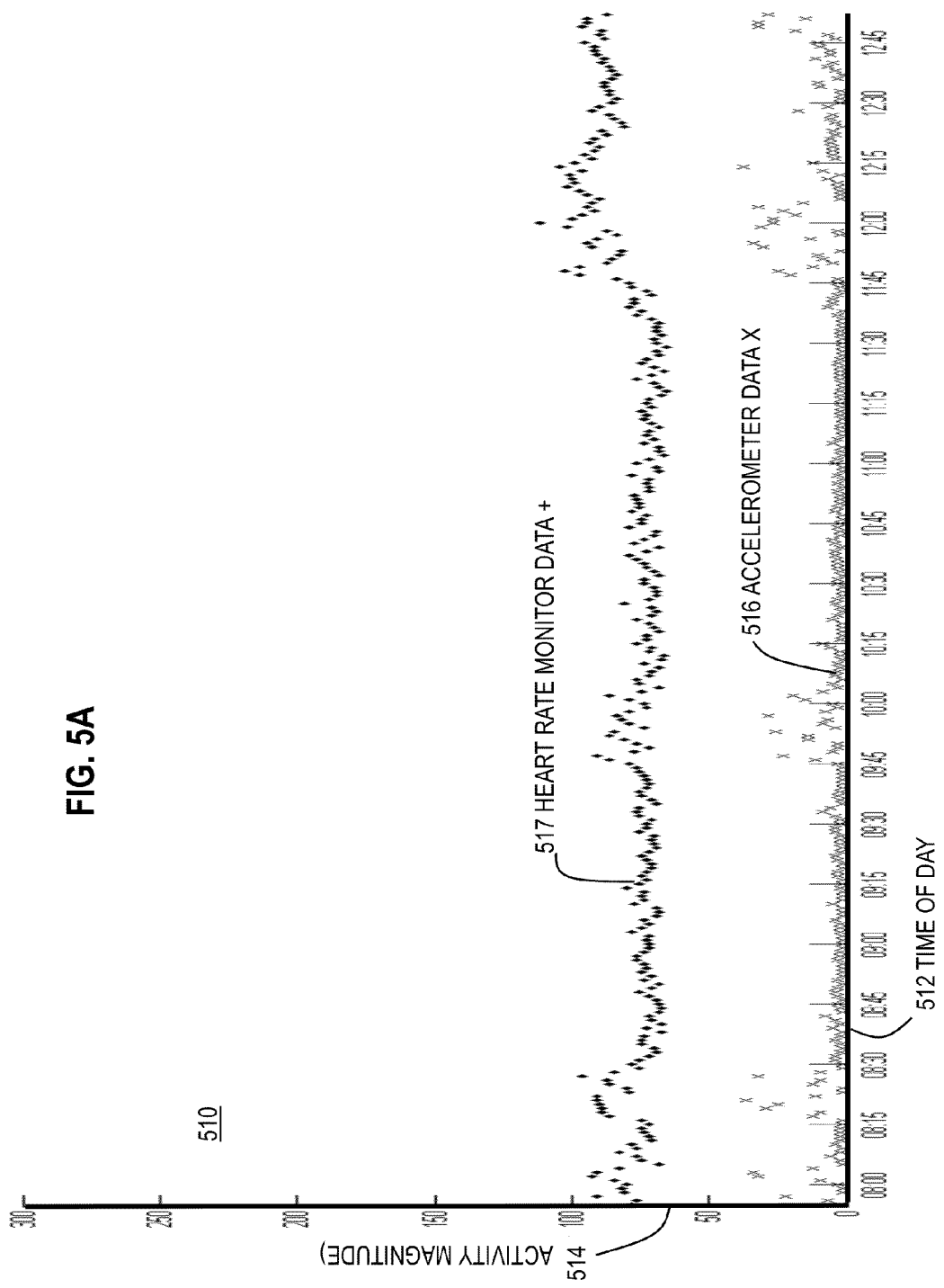
FIG. 5A is a graph that illustrates example heart rate monitor and accelerometer data, according to various embodiments.
Figure 5B:
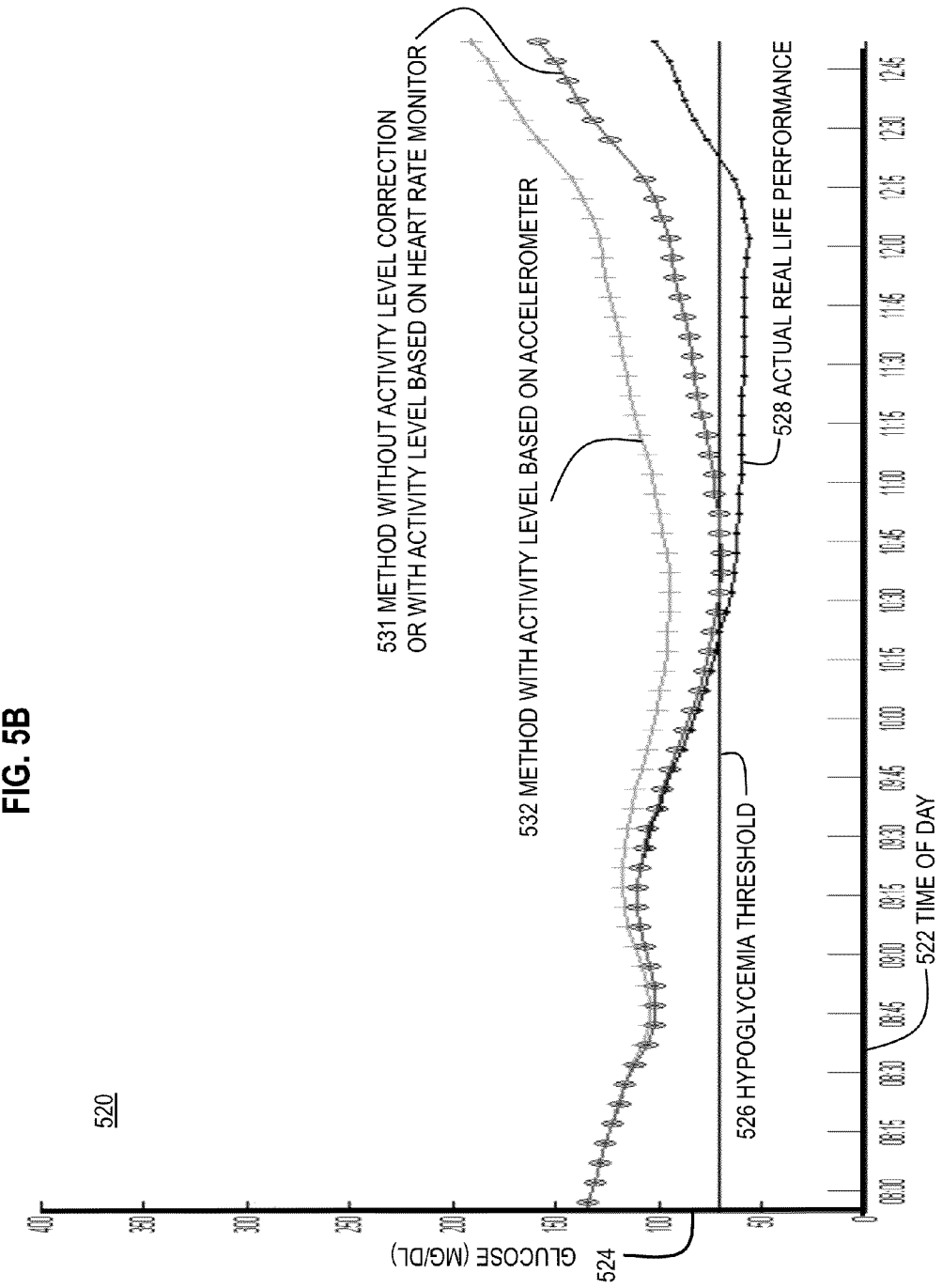
FIG. 5B is a graph that illustrates sample glucose trend traces during a morning of exercise, according to various embodiments.

FIG. 5A is a graph 510 that illustrates example heart rate monitor data 517 and accelerometer data 516, according to various embodiments. The horizontal axis 512 is time of day during the morning of observations; and, the vertical axis 514 is activity magnitude in units of each sensor. Periods of exercise are indicated by spikes in the data at about 8:15 AM, 9:45 AM and 11:45 AM, all more pronounced in the accelerometer data 516. In some embodiments, a constant value such as 60 subtracted from the HRM data 517 renders the HRM data percentage changes more dramatic. FIG. 5B is a graph 520 that illustrates sample glucose trend traces from a morning of exercise, according to various embodiments. The horizontal axis 522 is time of day; and, the vertical axis 524 is glucose reading in mg/dL. The hypoglycemia threshold 526 is plotted at 70 mg/dL. Trace 528 indicates the actual, real-life glucose experienced by the subject. Suspending the insulin pump, according to a first embodiment without step 217, produces trace 531. Suspending the insulin pump, according to a second embodiment with step 217 based on heart rate monitor data, produces essentially the same trace 531. Suspending the insulin pump, according to a third embodiment with step 217 based on accelerometer data, produces a superior trace 532. In this plot 520, there was no difference in the glucose trend using method 200 without step 217 and method 200 with step 217 based on HRM (trace 531), with the subject's CGM trend transiently grazing the 70 mg/dl line at about 10:30 AM. The embodiment with step 217 based on the accelerometer data (trace 532) was successful at preventing hypoglycemia altogether.

The simulator analysis suggest that, while the Kalman filter approach of some embodiments without activity level adjustments was moderately effective at mitigating hypoglycemia, when the method is informed with activity data, the ability of the embodiment to prevent hypoglycemia was improved. This enhancement may be particularly beneficial for people with T1D who are less inclined to make their own exercise-related insulin adjustments. Nine of the 22 patients wore the accelerometer/HRM during a week at diabetes camp, which encompasses a wide variety of activities and thus, a rich opportunity for monitoring. The remaining subjects were also from a wide spectrum of fitness backgrounds, including a mostly sedentary individual, a dancer, a collegiate athlete, a cyclist, and a marathon runner. Considering the diversity of subjects in regards to age and activities, the group does encompass a reasonable cross-section of the active population with T1D who would be most likely to benefit from an embodiment augmented with activity information.

For the simulator analysis, the 0.1 VMU and 90 bpm thresholds were selected to optimize the effectiveness of the embodiments using accelerometer and hear rate, respectively. Optimizing effectiveness means, for example, minimizing the number of hypoglycemic readings, while also limiting superfluous periods of suspension by maintaining the minutes of suspension per eliminated hypoglycemic reading to twice the level expected for the embodiments without step 217. The analysis, upon which these thresholds were based, includes histograms and other plots. The histograms demonstrated the frequency of readings above and below the 0.1 VMU and 90 bpm marks. Some other plots showed the number of hypoglycemic readings declines with lowering activity threshold; while, other plots show that decreasing activity threshold, increases the number of minutes of pump suspensions per hypoglycemic readings prevented. It is notable that participants spent a larger frequency of time with heart rates above the 90 bpm threshold than they did with accelerations above the 0.1 VMU. Numerous non-exercise phenomena (psychological stress, excitement, etc.) can also elevate the heart rate and this data is consistent with the published reports about inaccuracy of heart rate data alone as a marker of exercise.

It is noteworthy that a similar but unpublished study performed by others utilized a uni-axial accelerometer (without HRM) and obtained noisy, inconsistent acceleration readings that confounded attempts to reduce hypoglycemia through automatic pump suspension. By comparison, the data described herein suggest that: 1) in concert with previous findings, tri-axial accelerometers—such as the one used in the ZEPHYR BIOHARNESS™ 3—may provide more accurate data about the onset, duration, and intensity of activity than uni-axial accelerometers; and, 2) the more exercise one does (as in the case of the subjects at an active diabetes camp), the greater the likelihood of an accelerometer-augmented embodiment to be of benefit in decreasing one's risk of exercise-related hypoglycemia.

3.4 Experimental Embodiment D with Anomalous Measurement Detection

In this set of embodiments, the algorithm was modified to detect and ignore anomalous measurements from one or more sensors. For example, in an experimental embodiment, step 205 of the method 200 has been modified to avoid inappropriate pump suspensions in response to transient CGM signal attenuation (e.g., due to Pressure-Induced Sensor Attenuation, PISA). Furthermore, in this embodiment, pump suspensions (step 219) and subsequent re-starts (step 225) are performed automatically at the recommendation of the algorithm without any subject or operator interaction.

In an embodiment illustrated here, the prediction horizon H1 is 30 minutes rather than the 70 minutes of some previous embodiments. Furthermore, in this embodiment, the safety rules also include three additional rules, denoted herein as 3-1, 4-1 and 4-2 to show their position after rule 3 or rule 4 in the ranking of safety rules 1 to 6, described above.

(3-1) If the last continuous glucose measurement (CGM) reading is greater than the value one time step before, then it is determined to have the pump be on.

(4-1). If the last GCM reading is above a value for a threshold parameter Tmax (e.g., 230 mg/dl, or otherwise selected in a range from about 200 to about 400 mg/dl), then it is determined to have the pump be on.

(4-2). If the last CGM reading is less than the value one time step before by an absolute value that is more than a value for a change threshold parameter ΔCGMmax (nominally 40 mg/dl, or otherwise selected in a range from about 30 mg/dl to about 50 mg/dl), then it is determined to have the pump on. This is one way to protect against a negative sensor artifact.

In addition, if it is determined that a PISA is occurring, then CGM readings are not fed to the Kalman filter. For example, control stays in step 205 of method 200 until a next acceptable reading is obtained. In an illustrated embodiment, it is determined that a PISA has begun if the latest rate of change (ROC) for the CGM is less than (more negative than) −2 mg/dl and either: a) the previous ROC was than greater (more positive than) 0 mg/dl/min; or, b) the ratio of the current and last ROC is greater than 1.5. These conditions indicate that the rate of change is both sudden (e.g., rapidly decreasing), and significant. These conditions should not trigger for slowly developing drops in the glucose levels that gradually become rapid caused by a meal recovery or insulin correction bolus.

Once a PISA has been detected, the CGM values are not fed to the Kalman filter until one of the following conditions is true, ending the PISA, 1) The time in the PISA is greater than 240 minutes.
2) A sensor dropout is determined per rule 3 above.
3) The latest ROC is greater than −3.1 mg/di/min
   AND
   There have been exactly 4 readings in the PISA and the last two ROCs are within 20% of the ROC for 3 readings ago.
4) The latest ROC is greater than −3.1 mg/dl/min
   AND
   There have been exactly 5 readings in the PISA and the last two ROCs are within 20% of the ROC for 4 readings ago.
5) The latest ROC is greater than −3.1 mg/di/min
   AND
   The estimated glucose level is below the current reading.
6) There are three required sub-conditions here. The latest ROC is greater than −3.1 mg/dl/min.
   AND
   There have been at least 3 readings in the PISA.
   AND
   The last two second derivative estimates are negative. The second derivative, dROC(k), is calculated using Equation 14.

$$dROC(k) = ROC(k) - ROC(k-1)/(time(k) - time(k-1)). \quad (14)$$

The first rule is a straightforward limit on the number of readings that can be omitted. The second rule suggests that any substantial dropout will likely eliminate the cause of the PISA. The third and fourth rules seek to mitigate false positive detections from calibrations. The fifth rule reflects the fact that PISAs are attenuations and should result in a glucose estimate that is greater than the actual CGM values. Lastly, the sixth rule represents the detection of a PISA exit where the CGM values shoot up sharply and then "recover" to the actual glucose levels.

The tunable parameters are expanded in this embodiment as indicated in Table 5.

TABLE 5

Parameters for the Kalman Filter tuned in some embodiments.

| Param Name | Description | Unit | Allowable Values | Nominal Value |
|---|---|---|---|---|
| H | Prediction horizon for pump suspensions and restarts | min | 30, 40, 50, 60, 70 | 50 |
| $g_{off}$ | Predicted falling glucose threshold required for suspension | mg/dl | 70, 80, 90 | 80 |
| $T_{min}$ | Low glucose threshold required for suspension; treated as fixed parameter of 70 mg/dL | mg/dl | 60, 70, 80 | 70 |
| $T_{max}$ | High glucose threshold above which suspension is forbidden | mg/dl | none, 150, 180, 200, 230 | 230 |
| $\Delta CGM_{max}$ | Maximum CGM delta absolute value above which suspension is forbidden | mg/dl | none, 20, 30, 40, 50 | 40 |
| $g_{on}$ | Predicted rising glucose threshold required for pump restart after a suspension | mg/dl | 80, 90, 100, 110 | 100 |
| $ROC_{over}$ | Whether rising CGM can trigger a pump restart even if predicted glucose not yet above restart threshold | Yes/No | 1 (yes), 0 (no) | 1 |

TABLE 5-continued

Parameters for the Kalman Filter tuned in some embodiments.

| Param Name | Description | Unit | Allowable Values | Nominal Value |
|---|---|---|---|---|
| $ROC_{trump}$ | Whether rising CGM parameter "trumps" low threshold (i.e. can trigger a pump restart even if the current glucose is below the low glucose threshold) | Yes/ No | 1, 0 | 1 |
| r/q | Sensitivity of Kalman filter estimates to CGM readings | 1000 | 100, 1000, 10000 | 1000 |
| PISA Trigger | Rate-of-change trigger for Pressure-Induced Sensor Attenuation filter component | mg/dl/min | −2 (on), −100 (effectively disabled) | −2 |

4. PROCESSING HARDWARE OVERVIEW

FIG. 6 is a block diagram that illustrates a computer system 600 upon which an embodiment of the invention may be implemented. Computer system 600 includes a communication mechanism such as a bus 610 for passing information between other internal and external components of the computer system 600. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit.). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 600, or a portion thereof, constitutes a means for performing one or more steps of one or more methods described herein.

A sequence of binary digits constitutes digital data that is used to represent a number or code for a character. A bus 610 includes many parallel conductors of information so that information is transferred quickly among devices coupled to the bus 610. One or more processors 602 for processing information are coupled with the bus 610. A processor 602 performs a set of operations on information. The set of operations include bringing information in from the bus 610 and placing information on the bus 610. The set of operations also typically include comparing two or more units of information, shifting positions of units of information, and combining two or more units of information, such as by addition or multiplication. A sequence of operations to be executed by the processor 602 constitute computer instructions.

Computer system 600 also includes a memory 604 coupled to bus 610. The memory 604, such as a random access memory (RAM) or other dynamic storage device, stores information including computer instructions. Dynamic memory allows information stored therein to be changed by the computer system 600. RAM allows a unit of information stored at a location called a memory address to be stored and retrieved independently of information at neighboring addresses. The memory 604 is also used by the processor 602 to store temporary values during execution of computer instructions. The computer system 600 also includes a read only memory (ROM) 606 or other static storage device coupled to the bus 610 for storing static information, including instructions, that is not changed by the computer system 600. Also coupled to bus 610 is a non-volatile (persistent) storage device 608, such as a magnetic disk or optical disk, for storing information, including instructions, that persists even when the computer system 600 is turned off or otherwise loses power.

Information, including instructions, is provided to the bus 610 for use by the processor from an external input device 612, such as a keyboard containing alphanumeric keys operated by a human user, or a sensor. A sensor detects conditions in its vicinity and transforms those detections into signals compatible with the signals used to represent information in computer system 600. Other external devices coupled to bus 610, used primarily for interacting with humans, include a display device 614, such as a cathode ray tube (CRT) or a liquid crystal display (LCD), for presenting images, and a pointing device 616, such as a mouse or a trackball or cursor direction keys, for controlling a position of a small cursor image presented on the display 614 and issuing commands associated with graphical elements presented on the display 614.

In the illustrated embodiment, special purpose hardware, such as an application specific integrated circuit (IC) 620, is coupled to bus 610. The special purpose hardware is configured to perform operations not performed by processor 602 quickly enough for special purposes. Examples of application specific ICs include graphics accelerator cards for generating images for display 614, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 600 also includes one or more instances of a communications interface 670 coupled to bus 610. Communication interface 670 provides a two-way communication coupling to a variety of external devices that operate with their own processors, such as printers, scanners and external disks. In general the coupling is with a network link 678 that is connected to a local network 680 to which a variety of external devices with their own processors are connected. For example, communication interface 670 may be a parallel port or a serial port or a universal serial bus (USB) port on a personal computer. In some embodiments, communications interface 670 is an integrated services digital network (ISDN) card or a digital subscriber line (DSL) card or a telephone modem that provides an information communication connection to a corresponding type of telephone line. In some embodiments, a communication interface 670 is a cable modem that converts signals on bus 610 into signals for a communication connection over a coaxial cable or into optical signals for a communication connection over a fiber optic cable. As another example, communications interface 670 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 670 sends and receives electrical, acoustic or electromagnetic signals, including infrared and optical signals, that carry information streams, such as digital data.

The term computer-readable medium is used herein to refer to any medium that participates in providing information to processor 602, including instructions for execution. Such a medium may take many forms, including, but not limited to, non-volatile media, volatile media and transmission media. Non-volatile media include, for example, optical or magnetic disks, such as storage device 608. Volatile media include, for example, dynamic memory 604. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 602, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 602, except for carrier waves and other signals.

Logic encoded in one or more tangible media includes one or both of processor instructions on a computer-readable storage media and special purpose hardware, such as ASIC 320.

Network link 678 typically provides information communication through one or more networks to other devices that use or process the information. For example, network link 678 may provide a connection through local network 680 to a host computer 682 or to equipment 684 operated by an Internet Service Provider (ISP). ISP equipment 684 in turn provides data communication services through the public, world-wide packet-switching communication network of networks now commonly referred to as the Internet 690. A computer called a server 692 connected to the Internet provides a service in response to information received over the Internet. For example, server 692 provides information representing video data for presentation at display 614.

The invention is related to the use of computer system 600 for implementing the techniques described herein. According to one embodiment of the invention, those techniques are performed by computer system 600 in response to processor 602 executing one or more sequences of one or more instructions contained in memory 604. Such instructions, also called software and program code, may be read into memory 604 from another computer-readable medium such as storage device 608. Execution of the sequences of instructions contained in memory 604 causes processor 602 to perform the method steps described herein. In alternative embodiments, hardware, such as application specific integrated circuit 620, may be used in place of or in combination with software to implement the invention. Thus, embodiments of the invention are not limited to any specific combination of hardware and software.

The signals transmitted over network link 678 and other networks through communications interface 670, carry information to and from computer system 600. Computer system 600 can send and receive information, including program code, through the networks 680, 690 among others, through network link 678 and communications interface 670. In an example using the Internet 690, a server 692 transmits program code for a particular application, requested by a message sent from computer 600, through Internet 690, ISP equipment 684, local network 680 and communications interface 670. The received code may be executed by processor 602 as it is received, or may be stored in storage device 608 or other non-volatile storage for later execution, or both. In this manner, computer system 600 may obtain application program code in the form of a signal on a carrier wave.

Various forms of computer readable media may be involved in carrying one or more sequence of instructions or data or both to processor 602 for execution. For example, instructions and data may initially be carried on a magnetic disk of a remote computer such as host 682. The remote computer loads the instructions and data into its dynamic memory and sends the instructions and data over a telephone line using a modem. A modem local to the computer system 600 receives the instructions and data on a telephone line and uses an infra-red transmitter to convert the instructions and data to a signal on an infra-red a carrier wave serving as the network link 678. An infrared detector serving as communications interface 670 receives the instructions and data carried in the infrared signal and places information representing the instructions and data onto bus 610. Bus 610 carries the information to memory 604 from which processor 602 retrieves and executes the instructions using some of the data sent with the instructions. The instructions and data received in memory 604 may optionally be stored on storage device 608, either before or after execution by the processor 602.

FIG. 7 illustrates a chip set 700 upon which an embodiment of the invention may be implemented. Chip set 700 is programmed to perform one or more steps of a method described herein and includes, for instance, the processor and memory components described with respect to FIG. 6 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 700, or a portion thereof, constitutes a means for performing one or more steps of a method described herein.

In one embodiment, the chip set 700 includes a communication mechanism such as a bus 701 for passing information among the components of the chip set 700. A processor 703 has connectivity to the bus 701 to execute instructions and process information stored in, for example, a memory 705.

The processor 703 may include one or more processing cores with each core configured to perform independently. A multi-core processor enables multiprocessing within a single physical package. Examples of a multi-core processor include two, four, eight, or greater numbers of processing cores. Alternatively or in addition, the processor 703 may include one or more microprocessors configured in tandem via the bus 701 to enable independent execution of instructions, pipelining, and multithreading. The processor 703 may also be accompanied with one or more specialized components to perform certain processing functions and tasks such as one or more digital signal processors (DSP) 707, or one or more application-specific integrated circuits (ASIC) 709. A DSP 707 typically is configured to process real-world signals (e.g., sound) in real time independently of the processor 703. Similarly, an ASIC 709 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 703 and accompanying components have connectivity to the memory 705 via the bus 701. The memory 705 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 705 also stores the data associated with or generated by the execution of one or more steps of the methods described herein.

FIG. 8 is a diagram of exemplary components of a mobile terminal (e.g., handset) for communications, which is capable of operating in the system of FIG. 1, according to one embodiment. In some embodiments, mobile terminal 801, or a portion thereof, constitutes a means for performing one or more steps described herein. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory(ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 803, a Digital Signal Processor (DSP) 805, and a receiver/transmitter unit including a microphone gain control unit and a speaker gain control unit. A main display unit 807 provides a display to the user in support of various applications and mobile terminal functions that perform or support the steps as described herein. The display 807 includes display circuitry configured to display at least a portion of a user interface of the mobile terminal (e.g., mobile telephone). Additionally, the display 807 and display circuitry are configured to facilitate user control of at least some functions of the mobile terminal. An audio function circuitry 809 includes a microphone 811 and microphone amplifier that amplifies the speech signal output from the microphone 811. The amplified speech signal output from the microphone 811 is fed to a coder/decoder (CODEC) 813.

A radio section 815 amplifies power and converts frequency in order to communicate with a base station, which is included in a mobile communication system, via antenna 817. The power amplifier (PA) 819 and the transmitter/modulation circuitry are operationally responsive to the MCU 803, with an output from the PA 819 coupled to the duplexer 821 or circulator or antenna switch, as known in the art. The PA 819 also couples to a battery interface and power control unit 820.

In use, a user of mobile terminal 801 speaks into the microphone 811 and his or her voice along with any detected background noise is converted into an analog voltage. The analog voltage is then converted into a digital signal through the Analog to Digital Converter (ADC) 823. The control unit 803 routes the digital signal into the DSP 805 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WiFi), satellite, and the like, or any combination thereof.

The encoded signals are then routed to an equalizer 825 for compensation of any frequency-dependent impairments that occur during transmission though the air such as phase and amplitude distortion. After equalizing the bit stream, the modulator 827 combines the signal with a RF signal generated in the RF interface 829. The modulator 827 generates a sine wave by way of frequency or phase modulation. In order to prepare the signal for transmission, an up-converter 831 combines the sine wave output from the modulator 827 with another sine wave generated by a synthesizer 833 to achieve the desired frequency of transmission. The signal is then sent through a PA 819 to increase the signal to an appropriate power level. In practical systems, the PA 819 acts as a variable gain amplifier whose gain is controlled by the DSP 805 from information received from a network base station. The signal is then filtered within the duplexer 821 and optionally sent to an antenna coupler 835 to match impedances to provide maximum power transfer. Finally, the signal is transmitted via antenna 817 to a local base station. An automatic gain control (AGC) can be supplied to control the gain of the final stages of the receiver. The signals may be forwarded from there to a remote telephone which may be another cellular telephone, any other mobile phone or a land-line connected to a Public Switched Telephone Network (PSTN), or other telephony networks.

Voice signals transmitted to the mobile terminal 801 are received via antenna 817 and immediately amplified by a low noise amplifier (LNA) 837. A down-converter 839 lowers the carrier frequency while the demodulator 841 strips away the RF leaving only a digital bit stream. The signal then goes through the equalizer 825 and is processed by the DSP 805. A Digital to Analog Converter (DAC) 843 converts the signal and the resulting output is transmitted to the user through the speaker 845, all under control of a Main Control Unit (MCU) 803 which can be implemented as a Central Processing Unit (CPU) (not shown).

The MCU 803 receives various signals including input signals from the keyboard 847. The keyboard 847 and/or the MCU 803 in combination with other user input components (e.g., the microphone 811) comprise a user interface circuitry for managing user input. The MCU 803 runs a user interface software to facilitate user control of at least some functions of the mobile terminal 801 as described herein. The MCU 803 also delivers a display command and a switch command to the display 807 and to the speech output switching controller, respectively. Further, the MCU 803 exchanges information with the DSP 805 and can access an optionally incorporated SIM card 849 and a memory 851. In addition, the MCU 803 executes various control functions required of the terminal. The DSP 805 may, depending upon the implementation, perform any of a variety of conventional digital processing functions on the voice signals. Additionally, DSP 805 determines the background noise level of the local environment from the signals detected by microphone 811 and sets the gain of microphone 811 to a level selected to compensate for the natural tendency of the user of the mobile terminal 801.

The CODEC 813 includes the ADC 823 and DAC 843. The memory 851 stores various data including call incoming tone data and is capable of storing other data including music data received via, e.g., the global Internet. The software module could reside in RAM memory, flash memory, registers, or any other form of writable storage medium known in the art. The memory device 851 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 849 carries, for instance, important information, such as the cellular phone number, the carrier supplying service, subscription details, and security information. The SIM card 849 serves primarily to identify the mobile terminal 801 on a radio network. The card 849 also contains a memory for storing a personal telephone number registry, text messages, and user specific mobile terminal settings.

5. EXTENSIONS AND MODIFICATIONS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items. elements or steps. Furthermore, the indefinite article "a" or "an" is meant to indicate one or more of the item, element or step modified by the article.

7. REFERENCES

The entire contents of each of the following references are hereby incorporated by reference as if fully set forth herein, except for terminology that is inconsistent with that otherwise used herein.

1. Tsalikian E, Mauras N, Beck R W, Tamborlane W V, Janz K F, Chase H P, Wysocki T, Weinzimer S A, Buckingham B A, Kollman C, Xing D, Ruedy K J: Impact of exercise on overnight glycemic control in children with type 1 diabetes mellitus. J Pediatr 2005; 147:528-534.
2. Buckingham B, Beck R W, Tamborlane W V, Xing D, Kollman C, Fiallo-Scharer R, Mauras N, Ruedy K J, Tansey M, Weinzimer S A, Wysocki T: Continuous glucose monitoring in children with type 1 diabetes. J Pediatr 2007; 151:388-393, 393 e381-382.
3. Weinzimer S, Xing D, Tansey M, Fiallo-Scharer R, Mauras N, Wysocki T, Beck R, Tamborlane W, Ruedy K: FreeStyle navigator continuous glucose monitoring system use in children with type 1 diabetes using glargine-based multiple daily dose regimens: results of a pilot trial Diabetes Research in Children Network (DirecNet) Study Group. Diabetes Care 2008; 31:525-527.
4. The Juvenile Diabetes Research Foundation Continues Glucose Monitoring Study Group: Continuous glucose monitoring and intensive treatment of type 1 diabetes. N Engl J Med 2008; 359:1464-1476.
5. Buckingham B A, Cobry E, Clinton P, et al.: Preventing hypoglycemia using predictive alarm algorithms and insulin pump suspension. Diabetes Technol Ther 2009; 11:93-97.
6. Cameron F, Niemeyer G, Gundy-Burlet K, Buckingham B A: Statistical hypoglycemia prediction. J Diabetes Sci Technol 2008; 2:612-21.
7. Buckingham B, Chase H P, Dassau E, Cobry E, Clinton P, Gage V, Caswell K, Wilkinson J, Cameron F, Lee H, Bequette B W, Doyle F J $3^{rd}$: Prevention of Nocturnal Hypoglycemia Using Predictive Alarm Algorithms and Insulin Pump Suspension. Diabetes Care 2010; 33:1013-17.
8. Jones T W, Porter P, Sherwin R S, Davis E A, O'Leary P, Fraser F, Byrne G, Stick S, Tamborlane W V: Decreased epinephrine responses to hypoglycemia during sleep. N Engl J Med 1998; 338:1657-62.
9. Palerm C C, Bequette B W: Hypoglycemia detection and prediction using continuous glucose monitoring—a study on hypoglycemia clamp data. J Diabetes Sci Technol 2007; 1:617-23.
10. Palerm C C, Willis J P, Desemone J, Bequette B W: Hypoglycemia prediction and detection using optimal estimation. Diabetes Technol Ther 2005; 7:3-14.
11. Cameron F, Niemeyer G, Palerm C C, Dassay E, Doyle F J, Lee H, Bequette B W, Chase H P, Buckingham B A: Early detection of hypoglycemia combining multiple predictive methods on retrospective clinical continuous glucose monitoring data. J Diabetes Sci Technol 2008; 2:A19.
12. Cengiz E, Swan K L, Tamborlane W V, Steil G M, Steffen A T, Weinzimer S A: Is an automatic pump suspension feature safe for children with type 1 diabetes? An exploratory analysis with a closed-loop system. Diabetes Technol Ther 2009; 11:207-10.
13. Cameron F, Buckingham B, Wilson D, Chase H P, Lum J, Bequette B W: In-Patient Studies of a Predictive Low Glucose Suspend System. Presented at the $5^{th}$ International Conference on Advanced Technologies & Treatments for Diabetes, Barcelona, Spain, 8-11 Feb. 2012.
14. Cameron F, Wilson D M, Buckingham B A, Arzumanyan H, Clinton P, Chase H P, Lum J, Maahs D M, Calhoun P M, Bequette B W: Inpatient Studies of a Kalman-Filter-Based Predictive Pump Shutoff Algorithm. J Diabetes Sci Technol 2012; 6:196-201.
15. Buckingham B, Block J, Burdick J, Kalajian A, Kollman C, Choy M, Wilson D M, Chase P; Diabetes Research in Children Network. Response to nocturnal alarms using a real-time glucose sensor. Diabetes Technol Ther 2005; 7:440-47.
16. Juvenile Diabetes Research Foundation Continuous Glucose Monitoring Study Group. Prolonged nocturnal hypoglycemia is common during 12 months of continuous glucose monitoring in children and adults with type 1 diabetes. Diabetes Care. 2010; 33:1004-8.
17. Agrawal P, Welsh J B, Kannard B, Askari S, Yang Q, Kaufman F R. Usage and effectiveness of the low glucose suspend feature of the Medtronic Paradigm Veo insulin pump. J Diabetes Sci Technol 2011; 5:1137-41.
18. Choudhary P, Shin J, Wang Y, Evans M L, Hammond P J, Kerr D, Shaw J A, Pickup J C, Amiel S A. Insulin pump therapy with automated insulin suspension in response to hypoglycemia: reduction in nocturnal hypoglycemia in those at greatest risk. Diabetes Care 2011; 34:2023-5.
19. Dassau E, Cameron F, Lee H, Bequette B W, Zisser H, Jovanovic L, Chase H P, Wilson D M, Buckingham B A, Doyle F J 3rd. Real-time hypoglycemia prediction suite using continuous glucose monitoring: a safety net for the artificial pancreas. Diabetes Care 2010; 33:1249-54.
20. Knobbe E J, Buckingham B. The extended Kalman filter for continuous glucose monitoring. Diabetes Technol Ther. 2005; 7:15-27.
21. Bequette B W. Continuous glucose monitoring: real-time algorithms for calibration, filtering, and alarms. J Diabetes Sci Technol 2010; 4:404-18.
22. Facchinetti A, Sparacino G, Cobelli C. An online self-tunable method to denoise CGM sensor data. IEEE Trans Biomed Eng 2010; 57:634-41.
23. American Diabetes Association. Physical activity/exercise and diabetes. Diabetes Care 2004; 27(suppl 1):S58-S62.
24. Sonnenberg G E, Kemmer F W, Berger M. Exercise in type 1 (insulin-dependent) diabetic patients treated with continuous subcutaneous insulin infusion. Prevention of exercise induced hypoglycaemia. Diabetologia. 1990; 33(11):696-703.
25. Diabetes Research in Children Network (DirecNet) Study Group: The effects of aerobic exercise on glucose and counterregulatory hormone concentrations in children with type 1 diabetes. Diabetes Care 2006; 29:20-25.
26. MacDonald M J. Postexercise late-onset hypoglycemia in insulin-dependent diabetic patients. Diabetes Care 1987; 10:584-8.
27. Tuominen J A, Karonen S L, Melamies L, Bolli G, Koivisto V A. Exercise-induced hypoglycaemia in IDDM patients treated with a short-acting insulin analogue. Diabetologia 1995; 38:106-11.
28. Guelfi K J, Jones T W, Fournier P A. New insights into managing the risk of hypoglycaemia associated with intermittent highintensity exercise in individuals with type-1 diabetes mellitus. Sports Med 2007; 37:937-46.
29. Rabasa-Lhoret R, Bourque J, Ducros F, Chiasson J L. Guidelines for premeal insulin dose reduction for postprandial exercise of different intensities and durations in type 1 diabetic subjects treated intensively with a basal-bolus insulin regimen (ultralente-lispro). Diabetes Care 2001; 24:625-30.
30. Bernardini A L, Vanelli M, Chiari G, Iovane B, Gelmetti C, Vitale R, Errico M K. Adherence to physical activity in young people with type 1 diabetes. Acta Biomed 2004; 75:153-7.
31. Devadoss M, Kennedy L, Herbold N. Endurance athletes and type 1 diabetes. Diabetes Educ 2011; 37:193-207.
32. Diabetes Research in Children Network (DirecNet) Study Group, Tsalikian E, Kollman C, Tamborlane W B, Beck R W, Fiallo-Scharer R, Fox L, Janz K F, Ruedy K J, Wilson D, Xing D, Weinzimer S A. Prevention of hypoglycemia during exercise in children with type 1 diabetes by suspending basal insulin. Diabetes Care 2006; 29:2200-4.
33. Plasqui G, Westerterp K R. Physical activity assessment with accelerometers: an evaluation against doubly labeled water. Obesity. 2007; 15:2371-79.
34. Gradmark A, Pomeroy J, Renström F, Steiging a S, Persson M, Wright A, Bluck L, Domellöf M, Kahn S E, Mogren I, Franks P W. Physical activity, sedentary behaviors, and estimated insulin sensitivity and secretion in pregnant and non-pregnant women. BMC Pregnancy and Childbirth 2011; 11:44.
35. Balkau B, Mhamdi M, Oppert J M, Nolan J, Golay A, Porcellati F, Laakso M, Ferrannini E. Physical activity and insulin sensitivity. Diabetes 2008; 57:2613-18.
36. Ekelund U, Griffin S J, Wareham N J: Physical activity and metabolic risk in individuals with a family history of type 2 diabetes. Diabetes Care 2007; 30:337-42.
37. Simmons R K, Griffin S J, Steele R, Wareham N J, Ekelund U, the ProActive Research Team: Increasing overall physical activity and aerobic fitness is associated with improvements in metabolic risk: cohort analysis of the ProActive trial. Diabetologia 2008; 51:787-94.
38. Healy G N, Wijndaele K, Dunstan D W, Shaw J E, Salmon J, Zimmet P Z, Owen N: Objectively measured sedentary time, physical activity, and metabolic risk: the Australian Diabetes, Obesity and Lifestyle Study (AusDiab). Diabetes Care 2008; 31:369-71.
39. Arvidsson D, Fitch M, Hudes M L, Tudor-Locke C, Fleming S E. Accelerometer response to physical activity intensity in normal-weight versus overweight African American children. J Phys Act Health 2011; 8:682-92.
40. Cengiz E, Tamborlane W V. A tale of two compartments: interstitial versus blood glucose monitoring. Diabetes Technol Ther 2009; 11(Suppl 1):S11-6.
41. Livingstone M B, Prentice A M, Coward W A, Ceesay S M, Strain J J, McKenna P G, Nevin G B, Barker M E, Hickey R J. Simultaneous measurement of free-living energy expenditure by the doubly labeled water method and heart-rate monitoring. Am J Clin Nutr. 1990; 52:59-65.
42. Luke A, Maki K C, Barkey N, Cooper R, McGee D. Simultaneous monitoring of heart rate and motion to assess energy expenditure. Med Sci Sports Exerc 1997; 29:144-8.
43. Fudge B W, Wilson J, Easton C, Irwin L, Clark J, Haddow O, Kayser B, Pitsiladis Y P. Estimation of oxygen uptake during fast running using accelerometry and heart rate. Med Sci Sports Exerc 2007; 39:192-8.
44. Eston R G, Rowlands A V, Ingledew D K. Validity of heart rate, pedometry, and accelerometry for predicting the energy cost of children's activities. J Appl Physiol 1998; 84:362-71.
45. Frohnhauer M, Woodworth J, Anderson J. Graphical Human Insulin Time-Activity Profiles Using Standardized Definitions. Diabetes Technol Ther 2001; 3:419-29.
46. Swan K, Steffen A, Dziura J, Martin M, Steil G, Tamborlane W, Voskanyan G, Weinzimer S, Sikes K. Effect of Age of Infusion Site and Type of Rapid-Acting Analog on Pharmacodynamic Parameters of Insulin Boluses in Youth with Type 1 Diabetes Receiving Insulin Pump Therapy. Diabetes Care 2009; 32:240-4. doi: 10.2337/dc08-0595.

What is claimed is:
1. A non-transitory computer-readable medium carrying one or more sequences of instructions, wherein execution of the one or more sequences of instructions by one or more processors causes an apparatus to:
- determine values for a plurality of parameters for an automatic on-off switch for an insulin pump configured to inject insulin into a subject, wherein the plurality of parameters comprises a first prediction time horizon (H1), a first predicted glucose threshold (Goff) for turning the insulin pump off, a maximum shut off time within a first time window, and duration of the first time window;
- determine a safety rule based at least in part on the maximum shut off time within the first time window and the duration of the first time window;
- collect a plurality of glucose readings of a glucose level in a bloodstream of the subject up to a current time;
- determine an expected current glucose value G and expected current glucose temporal rate of change dG/dt based only on the plurality of glucose readings and a Kalman filter configured for noisy glucose readings of the glucose level in the bloodstream of the subject;
- predict a glucose level (Gh1) for a first future time that is the first prediction time horizon after the current time; and
- issue a command to shut off the insulin pump if it is determined both that the predicted glucose level (Gh1) is less than Goff and that the safety rule is satisfied.

2. The non-transitory computer-readable medium as recited in claim 1, wherein:
- the group of parameters further comprises a second predicted glucose threshold (Gon) for turning the insulin pump on, and a constant basal rate for the insulin pump when the insulin pump is on; and
- the apparatus is further configured to issue a command to turn on the insulin pump at the constant basal rate if it is determined both that the predicted glucose level (Gh1) is more than Gon and that the insulin pump is currently turned off.

3. The non-transitory computer-readable medium as recited in claim 2, wherein the second predicted glucose threshold (Gon) is in a range from about 90 milligram per deciliter to about 110 milligrams per deciliter.

4. The non-transitory computer-readable medium as recited in claim 1, wherein:
- the group of parameters further comprises a different second prediction time horizon, a predicted glucose threshold (Gon) for turning the insulin pump on, and a constant basal rate for the insulin pump when the insulin pump is on; and
- the apparatus is further configured to:
- predict a different glucose level (Gh2) for a different second future time that is the second prediction time horizon (H2) after the current time; and
- issue a command to turn on the insulin pump at the constant basal rate if it is determined both that the different predicted glucose level (Gh2) is more than Gon and that the insulin pump is currently turned off.

5. The non-transitory computer-readable medium as recited in claim 1, wherein:
- the group of parameters further comprises a maximum shut off time within a second time window and a duration of the second time window; and
- to determine the safety rule further comprises to determine the safety rule based at least in part on the maximum shut off time within the second time window and the duration of the second time window.

6. The non-transitory computer-readable medium as recited in claim 1, wherein:
- the group of parameters further comprises at least one of an initial variability of glucose readings, or initial variability in time rate of change of glucose, or a steady state variability of glucose values; and
- the Kalman filter is based at least in part on at least one of the values for the initial variability of glucose readings, or the initial variability in time rate of change of glucose, or the steady state variability of glucose values.

7. The non-transitory computer-readable medium as recited in claim 1, wherein:
- the group of parameters further comprises at least one of a default glucose value, or a prior multiplier, or a sensor dropout time; and
- the Kalman filter is based at least in part on at least one of the values for the default glucose value, or the prior multiplier, or the sensor dropout time.

8. The non-transitory computer-readable medium as recited in claim 1, wherein:
- the group of parameters further comprises a current activity level (Aoff) for turning the insulin pump off and a current glucose threshold (Ga) for turning the insulin pump off during activity; and
- the apparatus is further configured to
- collect a reading of activity level at the current time, and
- issue a command to shut off the insulin pump if it is determined both that the reading of activity level is more than Aoff and that the expected current glucose value G is less than Ga.

9. The non-transitory computer-readable medium as recited in claim 8, wherein the current glucose threshold (Ga) for turning the insulin pump off during activity is in about 180 milligrams per deciliter.

10. The non-transitory computer-readable medium as recited in claim 1, wherein
- the group of parameters further comprises a danger current glucose threshold (Gd) for turning off the insulin pump; and
- the safety rule is not satisfied if the expected current glucose value G is less than Gd.

11. The non-transitory computer-readable medium as recited in claim 1, wherein the first prediction time horizon H1 is in a range from about 50 minutes to about 90 minutes.

12. The non-transitory computer-readable medium as recited in claim 1, wherein the first predicted glucose threshold (Goff) is in a range from about 70 milligram per deciliter to about 90 milligrams per deciliter.

13. An apparatus comprising:
- at least one processor; and
- at least one memory including one or more sequences of instructions,
- the at least one memory and the one or more sequences of instructions configured to, with the at least one processor, cause the apparatus to perform at least the following,
- determining values for a plurality of parameters for an automatic on-off switch for an insulin pump configured to inject insulin into a subject, wherein the plurality of parameters comprises a first prediction time horizon, a predicted glucose threshold (Goff) for turning the insulin pump off, a maximum shut off time within a first time window, and duration of the first time window;
- determining a safety rule based at least in part on the maximum shut off time within the first time window and the duration of the first time window;
- collecting a plurality of glucose readings of a glucose level in a bloodstream of a subject up to a current time;
- determining an expected current glucose value G and expected current glucose temporal rate of change dG/dt based only on the plurality of glucose readings and a Kalman filter configured for noisy glucose readings of the glucose level in the bloodstream of the subject;

predicting a glucose level (Gh1) for a first future time that is the first prediction time horizon (H1) after the current time; and issuing a command to shut off the insulin pump if it is determined both that the predicted glucose level (Gh1) is less than Goff and that the safety rule is satisfied.

14. A method for operating an insulin pump, comprising:

determining values for a plurality of parameters for an automatic on-off switch for an insulin pump configured to inject insulin into a subject, wherein the plurality of parameters comprises a first prediction time horizon, a predicted glucose threshold (Goff) for turning the insulin pump off, a maximum shut off time within a first time window, and duration of the first time window;

determining a safety rule based at least in part on the maximum shut off time within the first time window and the duration of the first time window;

collecting a plurality of glucose readings of a glucose level in a bloodstream of a subject up to a current time;

determining an expected current glucose value G and expected current glucose temporal rate of change dG/dt based only on the plurality of glucose readings and a Kalman filter configured for noisy glucose readings of the glucose level in the bloodstream of the subject;

predicting a glucose level (Gh1) for a first future time that is the first prediction time horizon after the current time; and issuing a command to shut off the insulin pump if it is determined both that the predicted glucose level (Gh1) is less than Goff and that the safety rule is satisfied.

15. A system for operating an insulin pump, comprising:

means for determining values for a plurality of parameters for an automatic on-off switch for an insulin pump configured to inject insulin into a subject, wherein the plurality of parameters comprises a first prediction time horizon, a predicted glucose threshold (Goff) for turning the insulin pump off, a maximum shut off time within a first time window, and duration of the first time window;

means for determining a safety rule based at least in part on the maximum shut off time within the first time window and the duration of the first time window;

means for collecting a plurality of glucose readings of a glucose level in a bloodstream of a subject up to a current time;

means for determining an expected current glucose value G and expected current glucose temporal rate of change dG/dt based only on the plurality of glucose readings and a Kalman filter configured for noisy glucose readings of the glucose level in the bloodstream of the subject;

means for predicting a glucose level (Gh1) for a first future time that is the first prediction time horizon after the current time; and means for issuing a command to shut off the insulin pump if it is determined both that the predicted glucose level (Gh1) is less than Goff and that the safety rule is satisfied.

16. The system as recited in claim 15, further comprising:

means for determining a current activity level of the subject; and means for issuing a command to shut off the insulin pump if it is determined both that the current activity level exceeds a threshold value (Aoff), and that a second predicted glucose level (Gha) at a second time horizon (ha) after the current time is less than an glucose activity level threshold (Ga).

17. A non-transitory computer-readable medium carrying one or more sequences of instructions, wherein execution of the one or more sequences of instructions by one or more processors causes an apparatus to:

determine values for a plurality of parameters for an automatic on-off switch for an insulin pump configured to inject insulin into a subject, wherein the plurality of parameters comprises a first prediction time horizon (H1), a first predicted glucose threshold (Goff) for turning the insulin pump off, a maximum shut off time within a first time window, and duration of the first time window;

collect a plurality of glucose readings of a glucose level in a bloodstream of the subject up to a current time;

determine an expected current glucose value G and expected current glucose temporal rate of change dG/dt based only on the plurality of glucose readings and a Kalman filter configured for noisy glucose readings of the glucose level in the bloodstream of the subject;

predict a glucose level (Gh1) for a first future time that is the first prediction time horizon after the current time; and issue a command to shut off the insulin pump if it is determined that the predicted glucose level (Gh1) is less than Goff.

* * * * *